United States Patent
Tang et al.

(10) Patent No.: US 8,999,991 B2
(45) Date of Patent: Apr. 7, 2015

(54) INHIBITORS OF THE RENAL OUTER MEDULLARY POTASSIUM CHANNEL

(71) Applicants: Haifeng Tang, Metuchen, NJ (US); Barbara Pio, West Orange, NJ (US); Harry R. Chobanian, Aberdeen, NJ (US)

(72) Inventors: Haifeng Tang, Metuchen, NJ (US); Barbara Pio, West Orange, NJ (US); Harry R. Chobanian, Aberdeen, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/353,418

(22) PCT Filed: Oct. 22, 2012

(86) PCT No.: PCT/US2012/061296
§ 371 (c)(1),
(2) Date: Apr. 22, 2014

(87) PCT Pub. No.: WO2013/062900
PCT Pub. Date: May 2, 2013

(65) Prior Publication Data
US 2014/0288088 A1    Sep. 25, 2014

Related U.S. Application Data

(60) Provisional application No. 61/550,956, filed on Oct. 25, 2011.

(51) Int. Cl.
| | |
|---|---|
| A61K 31/495 | (2006.01) |
| A61K 31/496 | (2006.01) |
| C07D 295/22 | (2006.01) |
| C07D 401/04 | (2006.01) |
| C07D 405/06 | (2006.01) |
| C07D 405/14 | (2006.01) |
| C07D 417/14 | (2006.01) |
| C07D 241/04 | (2006.01) |
| A61K 45/06 | (2006.01) |
| C07D 409/14 | (2006.01) |
| C07D 495/04 | (2006.01) |

(52) U.S. Cl.
CPC ............ *C07D 405/14* (2013.01); *C07D 241/04* (2013.01); *A61K 31/495* (2013.01); *A61K 31/496* (2013.01); *A61K 45/06* (2013.01); *C07D 405/06* (2013.01); *C07D 409/14* (2013.01); *C07D 417/14* (2013.01); *C07D 495/04* (2013.01)

(58) Field of Classification Search
None
See application file for complete search history.

(56) References Cited

U.S. PATENT DOCUMENTS

| | | |
|---|---|---|
| 2,988,551 A | 6/1961 | Morren |
| 3,435,002 A | 3/1969 | Holub |
| 3,632,608 A | 1/1972 | Holub |
| 3,749,722 A | 7/1973 | Holub |
| 4,579,863 A | 4/1986 | Horwell et al. |
| 4,806,536 A | 2/1989 | Cross et al. |
| 4,992,547 A | 2/1991 | Berner et al. |
| 5,145,885 A | 9/1992 | Berner et al. |
| 5,215,989 A | 6/1993 | Baldwin et al. |
| 5,614,526 A | 3/1997 | Godel et al. |
| 5,736,546 A | 4/1998 | Kawashima et al. |
| 6,258,813 B1 | 7/2001 | Arlt et al. |
| 6,787,543 B2 | 9/2004 | Take et al. |
| 2004/0204404 A1 | 10/2004 | Zelle et al. |
| 2005/0215526 A1 | 9/2005 | Hulme et al. |
| 2005/0267121 A1 | 12/2005 | Li et al. |
| 2006/0183739 A1 | 8/2006 | Tsaklakidis et al. |
| 2006/0183742 A1 | 8/2006 | Mederski et al. |
| 2006/0211692 A1 | 9/2006 | Mederski et al. |
| 2007/0004750 A1 | 1/2007 | Lorsbach et al. |
| 2007/0093472 A1 | 4/2007 | Mederski et al. |
| 2007/0232546 A1 | 10/2007 | Sharma et al. |
| 2008/0003214 A1 | 1/2008 | Cezanne et al. |
| 2010/0286123 A1 | 11/2010 | Pasternak et al. |

FOREIGN PATENT DOCUMENTS

| | | |
|---|---|---|
| EP | 0099148 B1 | 2/1988 |
| EP | 0175376 B1 | 4/1991 |
| EP | 1094063 A1 | 4/2001 |
| EP | 1939175 A1 | 7/2009 |

(Continued)

OTHER PUBLICATIONS

Felix et al. Assay and Drug Development Technologies,10(5),pp. 417-431 (2012).*

(Continued)

*Primary Examiner* — Emily Bernhardt
(74) *Attorney, Agent, or Firm* — Nicole M. Beeler; Catherine D. Fitch

(57) ABSTRACT

The present invention provides compounds of Formula I

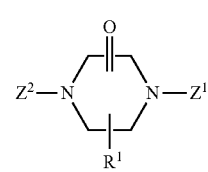

and the pharmaceutically acceptable salts thereof, which are inhibitors of the ROMK (Kir1.1) channel. The compounds act as diuretics and natriuretics and are valuable pharmaceutically active compounds for the therapy and prophylaxis of medical conditions including cardiovascular diseases such as hypertension and conditions resulting from excessive salt and water retention.

14 Claims, No Drawings

(56) References Cited

FOREIGN PATENT DOCUMENTS

| | | |
|---|---|---|
| FR | 2673182 | 8/1992 |
| GB | 949088 A | 2/1964 |
| GB | 1575310 A | 9/1980 |
| GB | 2116967 | 7/1986 |
| JP | 10203986 | 8/1998 |
| WO | 9744329 | 11/1997 |
| WO | 0051611 A1 | 9/2000 |
| WO | 0232874 | 4/2002 |
| WO | 0204314 A1 | 6/2002 |
| WO | 0250061 A1 | 6/2002 |
| WO | 2004020422 A1 | 3/2004 |
| WO | 2004037817 A1 | 5/2004 |
| WO | 2004046110 | 6/2004 |
| WO | 2005037843 | 4/2005 |
| WO | 2005044797 | 5/2005 |
| WO | 2006034341 A2 | 3/2006 |
| WO | 2006034769 A1 | 4/2006 |
| WO | 2006098342 A1 | 9/2006 |
| WO | 2006129199 A1 | 12/2006 |
| WO | 2007075629 A2 | 7/2007 |
| WO | 2008147864 | 12/2008 |
| WO | 2008147864 A2 | 12/2008 |
| WO | 2009149508 | 11/2009 |
| WO | 2010129379 A1 | 11/2010 |
| WO | 2012058116 A1 | 5/2012 |
| WO | 2012058134 A1 | 5/2012 |
| WO | 2013028474 A1 | 2/2013 |
| WO | 2013039802 A1 | 3/2013 |
| WO | 2013062892 A1 | 5/2013 |
| WO | 2013066714 A1 | 5/2013 |
| WO | 2013066717 A1 | 5/2013 |
| WO | 2013066718 A2 | 5/2013 |
| WO | 2013090271 A1 | 6/2013 |
| WO | 2014015495 A1 | 1/2014 |
| WO | 2014018764 A1 | 1/2014 |

OTHER PUBLICATIONS

ACCF/AHA Practice Guideline, 2009 Focused update incorporated into the ACC/AHA 2005 guidelines . . . , Circulation, 2009, e391-e436, 119.
Baltzly, R., The preparation of N-mono-substituted and unsymmetrically disubstituted piperazines, J. Am. Chemoc., 1944, 263-266, 66.
Bhave, G., Small-molecule modulators of inward rectifier K+ channels: recent advances and future possibilities, Future Med Chem, 2010, 757-774, 2(5).
Bhave,G., Development of a selective small-molecule inhibitor Kir1.1, the renal outer medullary potassium channel, Mol. Pharmacol., 2011, 42-50, 79.
Brater et al., Diuretic Therapy, Drug Therapy, 1998, 387-395, 339.
Brewster et al., Antihypertensive 1,4-bis (2-indol-3-ylethyl)piperazines, Chimie Ther., 1973, 169-172 (English trans.), 2.
Cerkvenik-Flajs V, Determination of residues of azaperone in the kidneys by liquid chromatography with fluorescence, Anal. Chim. Acta., 2007, 374-382, 586.
Chemical Abstracts (2004), Abstract No. 697771-49-6, "1,3-lsobenzofurandione 5-[[4-[(5-chloro-2-methoxyphenyl) sulfonyl]-1- . . . ".
Cheymol et al., Increase in the effects of epinephrine and acetylcholine . . . , Comptes Rendus des seances de la Societe de Biologie, 1951, 496-499 (English trans.), 145.
Fallen, K., The Kir channel immunoglobuling domain is essential for Kir1.1 (ROMK) thermodynamic stability, trafficing and gating, Channels, 2009, 57-66, 3.
Felker et al, Diuretic strategies in patients with acute decompensated heart failure, New Eng. J. Med., 2011, 797-805, 364.
Frank, Managing hypertension using combination therapy, Am. Fam. Physician, 2008, 1279-1286, 77.
International Search Report of PCT/US2012/61296 mailed Jan. 7, 2013, 8 pages.
Kulkarni, YD, Possible antifertility agents, part III. Synthesis of 4-(substituted aminomethyl)-5,6,7-trimethoxy phthalid . . . (abstract)), Biol. Mem., 1987, 141-144, 13.
Lanyi et al., Piperazine-Derivatives II, Res. Lab. of Chinoin-Fabrik Chemisch-Pharma. Prod., 1968, 1431-1435 (English trans.), 18.
Lee et al, Functional and structural characterization of PKA-mediated pHi gating of ROMK1 channels, Journal of Molecular Graphics and Modelling, 2008, 332-341, 27.
Lewis, L. M., High-throughput screening reveals a small-molecule inhibitor of the Renal Outer Medullary Potassium Channel and Kir7.1, Mol. Pharncol., 2009, 1094-1103, 76.
Lutz, R. E., Antimalarials. Some Piperazine Derivatives, J. Org. Chem., 1947, 771-775, 12, BO.
Miyake et al., Synthesis of 1-substituted isochroman . . . , Takeda Res. Lab., 1982, 24-40 (English trans.), 41.
Sica, D. A., Diuretic use in renal disease, Nature, 2012, 100-109, 8.
Zejc et al., Piperazine derivative of dimethylxanthines, Polish J. Pharmacol. & Pharm., 1975, 311-316 (English trans.), 27.

* cited by examiner

INHIBITORS OF THE RENAL OUTER MEDULLARY POTASSIUM CHANNEL

CROSS REFERENCE TO RELATED APPLICATIONS

This application is a U.S. National Phase application under 35 U.S.C. §371 of PCT Application No. PCT/US12/061296 filed Oct. 22, 2012, which claims priority from U.S. Provisional Application Ser. No. 61/550,956, filed Oct. 25, 2011.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are predicted to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first publicly disclosed small molecule selective inhibitors of ROMK, including VU590, were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. The compound VU591 was later reported in Bhave, G. et al., *Development of a Selective Small-Molecule Inhibitor of Kir1.1, the Renal Outer Medullary Potassium Channel*, Mol Pharmacol, 2011, 79(1), p. 42-50, the text of which states that "ROMK (Kir1.1), is a putative drug target for a novel class of loop diuretics that would lower blood pressure without causing hypokalemia."

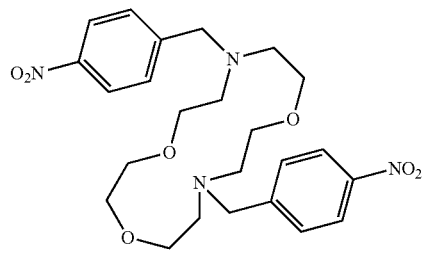

VU590

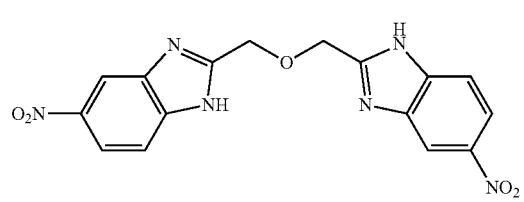

VU591

Patent application publication number WO2010/129379, published Nov. 11, 2010 having common representative Merck Sharp & Dohme Corp., (also published as US2010/0286123 on same date), describes ROMK inhibitors having the generic formula:

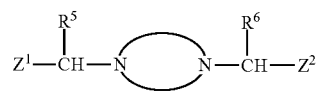

and, e.g., an embodiment

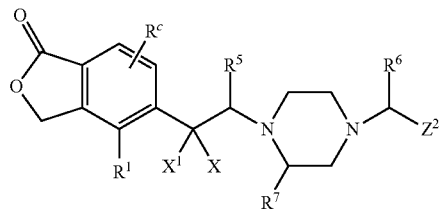

wherein $R^5$ and $R^6$ are independently —H, —$C_{1-6}$ alkyl, —$C_{3-6}$ cycloalkyl, —$CF_3$, —$CHF_2$, —$CH_2F$ or —$CH_2OH$; X is —H, —OH, —$OC_{1-3}$alkyl, —F, oxo, $NH_2$ or —$CH_3$; and $X^1$ is —H or —$CH_3$.

Patent application publication number WO2012/058134, published May 3, 2012, having common representative Merck Sharp & Dohme Corp., describes ROMK inhibitors having the generic formula:

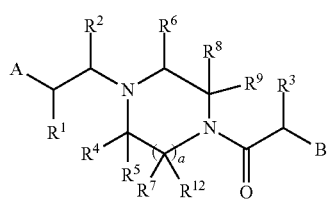

wherein A and B are mono and/or bicyclic aromatic groups; $R^2$ is —H, —$C_{1-6}$ alkyl, —$C_{3-6}$ cycloalkyl, $CF_3$, —$CH_2OH$, or —$CO_2R$, or $R^2$ can be joined to $R^1$ or $R^{10a}$ to form a ring; $R^3$ is —H, —$C_{1-6}$ alkyl, —$C_{3-6}$ cycloalkyl, —OH, —F, —$OC_{1-3}$ alkyl, or —$CH_2OH$, or $R^3$ can be joined to $R^{10b}$ to form a ring.

Patent application publication number WO2012/058116, published May 3, 2012, having common representative Merck Sharp & Dohme Corp., describes ROMK inhibitors having the generic formula:

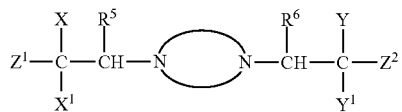

and, e.g., an embodiment

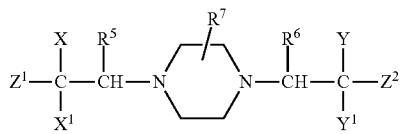

wherein $R^5$ and $R^6$ are independently —H, —$C_{1-6}$ alkyl or —$C(O)OC_{1-3}$alkyl; and X, $X^1$, Y and $Y^1$ are independently —H or —$C_{1-6}$alkyl; or $Y^1$ can be joined together with $Z^2$ to form a fused ring system.

However, continuing discovery of selective small molecule inhibitors of ROMK is still needed for the development of new treatments for hypertension and related disorders. The compounds of Formula I and salts thereof of this invention are selective inhibitors of the ROMK channel and could be used for the treatment of hypertension, heart failure and other conditions where treatment with a diuretic or natriuretic would be beneficial.

SUMMARY OF THE INVENTION

The present invention provides compounds of Formula I, defined herein, and the pharmaceutically acceptable salts thereof. The compounds of Formula I are inhibitors of the ROMK (Kir1.1) channel. As a result, the compounds of Formula I could be used in methods of treatment, inhibition or amelioration of one or more disease states that could benefit from inhibition of ROMK. The compounds of this invention could be used in methods of treatment which comprise administering a therapeutically or prophylactically effective amount of a compound of Formula I to a patient in need of a diuretic and/or natriuretic agent. Therefore, the compounds of Formula I could be valuable pharmaceutically active compounds for the therapy, prophylaxis or both of medical conditions, including, but not limited to, cardiovascular diseases such as hypertension and heart failure, and conditions associated with excessive salt and water retention. The compounds of this invention could further be used in combination with other therapeutically effective agents, including but not limited to, other drugs which are useful for the treatment of hypertension, heart failure and conditions associated with excessive salt and water retention. The invention furthermore relates to processes for preparing compounds of Formula I, and pharmaceutical compositions which comprise compounds of Formula I. These and other aspects of the invention will be evident from the description contained herein.

DETAILED DESCRIPTION OF THE INVENTION

The present invention is directed to compounds having structural Formula I:

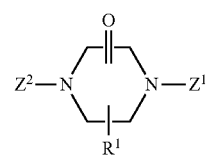

I and the pharmaceutically acceptable salts thereof wherein:
$Z^1$ is

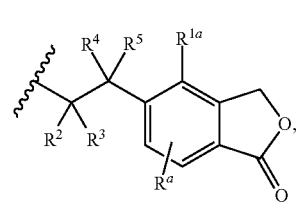

z1-a

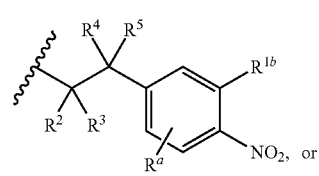

z1-b

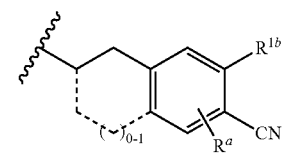

z1-c wherein the dashed bonds represent the optional presence of —$C_{1-2}$alkanediyl- which, when present, forms a 5 to 6 membered carbocyclic ring which is fused to the aryl ring;

$Z^2$ is

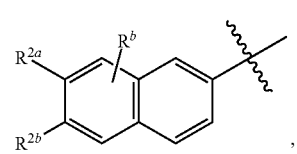

z2-a

-continued

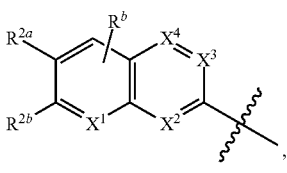
z2-b

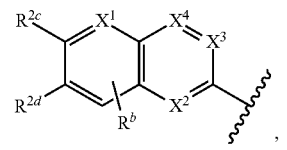
z2-c

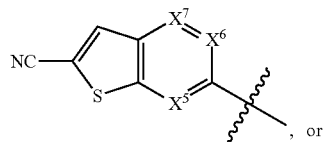
, or z2-d

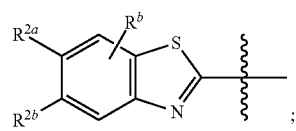
;
z2-e

R$^1$ is —H, —CH$_3$, —CF$_3$, —CHF$_2$, —CH$_2$F or —CH$_2$OH;
R$^2$ is —H, oxo (=O) or —C$_{1-6}$alkyl;
R$^4$ is —H, —OH, oxo or —C$_{1-6}$alkyl;
  provided that when R$^4$ is —OH or oxo, then R$^2$ is not oxo;
R$^3$ and R$^5$ are each independently —H or —C$_{1-6}$alkyl; provided that R$^3$ is absent when R$^2$ is oxo, and R$^5$ is absent when R$^4$ is oxo;
R$^{1a}$ is —H, halo or —C$_{1-3}$alkyl;
R$^{1b}$ is —H, halo, —C$_{1-3}$ alkyl, —O—C$_{1-3}$ alkyl or —COOC$_{1-3}$ alkyl;
one of R$^{2a}$ and R$^{2b}$ is —CN and the other is —H or —C$_{1-3}$alkyl;
one of R$^{2c}$ and R$^{2d}$ is —SO$_2$—C$_{1-3}$alkyl and the other is —H or —C$_{1-3}$alkyl;
X$^1$, X$^2$, X$^3$ and X$^4$ are each independently CH or N, provided that only one of X$^1$, X$^2$, X$^3$ or X$^4$ is N;
X$^5$, X$^6$ and X$^7$ are each independently CH or N, provided that only one of XS, X$^6$ or X$^7$ is N; and
R$^a$ and R$^b$ are each independently —H, halo, —C$_{1-3}$alkyl, —O—C$_{1-3}$alkyl or —COOC$_{1-3}$alkyl.

The present invention is further directed to compounds of Formula I having structural Formula II:

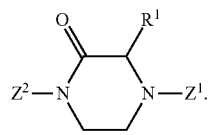
II

In another embodiment of this invention are compounds of Formula I or II wherein Z$^1$ is z1-a. In a class thereof are compounds wherein R$^2$, R$^3$ and R$^5$ are each —H, and R$^4$ is —H, —OH or oxo, and more particularly R$^4$ is —H or —OH. In a sub-class are compounds wherein R$^1$ is —H.

In another embodiment of this invention are compounds of Formula I or II wherein Z$^1$ is z1-b. In a class thereof are compounds wherein R$^2$, R$^3$ and R$^5$ are each —H, and R$^4$ is —H, —OH or oxo, and more particularly R$^4$ is —H or —OH. In a sub-class are compounds wherein R$^1$ is —H.

In another embodiment of this invention are compounds of Formula I or II wherein Z$^1$ is z1-c. In a class thereof are compounds wherein the dashed bonds in z1-c represent —C$_{1-2}$alkanediyl- and z1-c has the formula z1-c1:

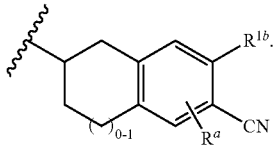
z1-c1

In another class thereof are compounds wherein the dashed bonds in z1-c are absent and therefore —C$_{1-2}$alkanediyl- is not present, and z1-c has the formula z1-c2:

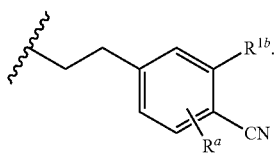
z1-c2

In a sub-class of both classes are compounds wherein R$^1$ is —H.

All structural Formulas and embodiments described herein include the pharmaceutically acceptable salts of the compounds defined therein.

As used herein except if noted otherwise, "alkyl" is intended to include both branched- and straight-chain saturated aliphatic hydrocarbon groups having the specified number of carbon atoms. Commonly used abbreviations for alkyl groups are used throughout the specification. For example the term "C$_{1-6}$ alkyl" (or "C$_1$-C$_6$ alkyl"), means linear or branched chain alkyl groups, including all isomers, having the specified number of carbon atoms and includes all of the hexyl and pentyl isomers as well as n-, iso-, sec- and tert-butyl (butyl, s-butyl, i-butyl, t-butyl; Bu=butyl), n- and i-propyl (Pr=propyl), ethyl (Et) and methyl (Me). Halo means —F, —Cl, —Br and —I. In the Formula I, preferred halos are —F and —Cl.

As used herein "alkanediyl" is a saturated aliphatic divalent hydrocarbon group having the specified number of carbon atoms. Examples of alkanediyl groups include, but are not limited to, methanediyl, ethanediyl, propanediyl, butanediyl and the like. The term —C$_{1-2}$alkanediyl- describes methanediyl or ethanediyl.

Unless expressly depicted or described otherwise, variables depicted in a structural formula with a "floating" bond, such as R$^1$, are permitted on any available carbon atom in the ring to which the variable is attached.

The present invention encompasses all stereoisomeric forms of the compounds of Formula I. Centers of asymmetry that are present in the compounds of Formula I can all independently of one another have (R) or (S) configuration. When bonds to the chiral carbon are depicted as straight lines in the structural Formulas of the invention, or when a compound name is recited without a chiral designation for a chiral carbon, it is understood that both the (R) and (S) configurations of the chiral carbon and hence both enantiomers and mixtures thereof, are embraced within the Formula or by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (which includes hydrates) and solvated salts of such racemates, enantiomers, diastereomers and tautomers and mixtures thereof.

Reference to the compounds of Formula I herein encompasses the compounds of Formula II and all embodiments thereof. Reference to the compounds of this invention as those of a specific formula or embodiment or any other generic structural formula or specific compound described or claimed herein, is intended to encompass the specific compound or compounds falling within the scope of the Formula or embodiment, including salts thereof, particularly pharmaceutically acceptable salts, solvates (including hydrates) of such compounds and solvated (or hydrated) salt forms thereof, where such forms are possible unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding pharmaceutically acceptable salts. Thus, the compounds of Formula I which contain acidic groups can be used according to the invention, for example, as alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO⁻ depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula I in a ROMK-inhibitory effective amount to a patient in need thereof. The inhibition of ROMK by the compounds of Formula I can be examined, for example, in the Thallium Flux Assay described below. Moreover, this invention also relates to the use of the compounds of Formula I or salts thereof to validate in vitro assays, for example but not limited to the Thallium Flux Assay described herein.

The compounds of this invention could be used in a method for causing diuresis, natriuresis or both, comprising administering a compound of Formula I in a therapeutically effective amount to a patient in need thereof. Therefore, the compounds of Formula I of this invention could be used in methods for treatment of, prevention of or reduction of risk for developing medical conditions that benefit from increased excretion of water and sodium, such as but not limited to one or more of hypertension, heart failure (both acute and chronic, the latter also known as congestive heart failure) and/or other conditions associated with excessive salt and water retention. Furthermore, the compounds of Formula I could be used in methods for treatment of, prevention of or reduction of risk for developing one or more disorders such as pulmonary arterial hypertension (PAH), cardiovascular disease, diabetes mellitus, diabetes insipidus, post-operative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, glomerulonephritis, nephrotic syndrome, acute and chronic kidney insufficiency (also referred to as chronic kidney disease, or more generally as renal impairment), acute tubular necrosis, hypercalcemia, idiopathic edema, Dent's disease, Meniere's disease, edematous states, glaucoma, benign intracranial hypertension, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

The compounds of Formula I may potentially have reduced liabilities (for example, hypo- or hyperkalemia, new onset of diabetes, dyslipidemia, etc.) over currently used clinical agents. Also the compounds may have reduced risk for diuretic tolerance, which can be a problem with long-term use of loop diuretics.

In general, compounds that are ROMK inhibitors can be identified as those compounds which, when tested, have an $IC_{50}$ of 5 µM or less, preferably 1 µM or less, and more preferably 0.25 µM or less, in the Thallium Flux Assay, which is described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of bodyweight) is appropriate for administration to an adult weighing approximately 75 kg in order to obtain the desired results. The daily dose is preferably administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the individual response, it may be necessary to deviate upwards or downwards from the given daily dose. Furthermore, the compound may be formulated for immediate or modified release such as extended or controlled release.

The term "patient" includes animals, preferably mammals and especially humans, who use the instant active agents for the prohylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention or reduction of risk of myocardial infarction or prevention and reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula I and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants.

Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from 0.1 to 200 mg, particularly from 0.1 to 100 mg, and more particularly from 0.1 to 50 mg, per dose on a free acid/free base weight basis, but depending on the type of the pharmaceutical composition, potency of the active ingredient and/or the medical condition being treated, it could also be lower or higher. Pharmaceutical compositions usually comprise 0.5 to 90 percent by weight of the active compound on a free acid/free base weight basis.

The compounds of Formula I inhibit ROMK. On account of this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. The additional active agent (or agents) is intended to mean a medicinal compound that is different from the compound of Formula I, and which is a pharmaceutically active agent (or agents) that is active in the body, including pro-drugs, for example esterified forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of the one or more additional active agents which may be employed include but are not limited to thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVANHCT®, ATACAND HCT®), etc.); potassium sparing diuretics such as amiloride HCl, spironolactone, epleranone, triamterene, each with or without HCTZ; carbonic anhydrase inhibitors, such as acetazolamide, neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, gallopamil, niludipine, nimodipine, nicardipine, bepridil, nisoldipine); potassium channel activators (e.g., nicorandil, pinacidil, cromakalim, minoxidil, aprilkalim, loprazolam); sympatholytics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds eg isosorbide mononitrate, lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms, pro-drug forms including but not limited to esters, and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I, or the active agent(s) therein could be used in a fixed dose drug combination including a compound of Formula I.

Several methods for preparing the compounds of this invention are described in the examples. Starting materials and intermediates are purchased, made from known procedures, or as otherwise illustrated. Some frequently applied routes to the compounds of Formula I are also described by the Schemes as follows. In some cases the order of carrying out the steps of reaction schemes may be varied to facilitate the reaction or to avoid unwanted reaction products. The Ar group shown in the below schemes can represent any of the mono- or bi-cyclic rings at the terminal end of $Z^1$ as defined previously.

Two general methods were used for the synthesis of the compounds of Formula I. As shown In Scheme 1, N-Boc piperazine 1-1 may be coupled to $Z^2$-Halide (Halide=Cl, Br, or I) under palladium catalysis conditions (Buchwald, et. al. *Organic Letters,* 2000, 2(8), 1101-1104.). The Boc group of 1-2 was then removed to afford amine 1-3, which was reacted with electrophile 1-4 or 1-5 to deliver compounds of formula II-1 or II-2, respectively. Alternatively, keto-piperazine 1-6 was first reacted with epoxide 1-7 to furnish carboxamide 1-8, which was further coupled to $Z^2$-Halide under palladium catalysis conditions to provide compounds of formula II-2, as shown in Scheme 2.

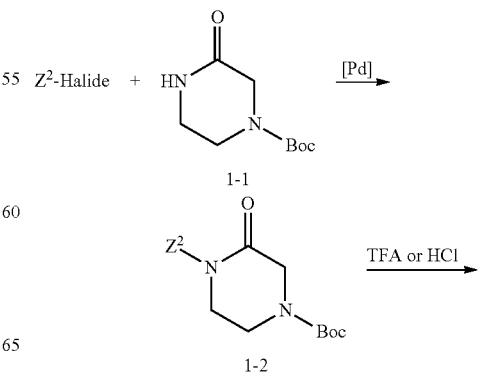

-continued

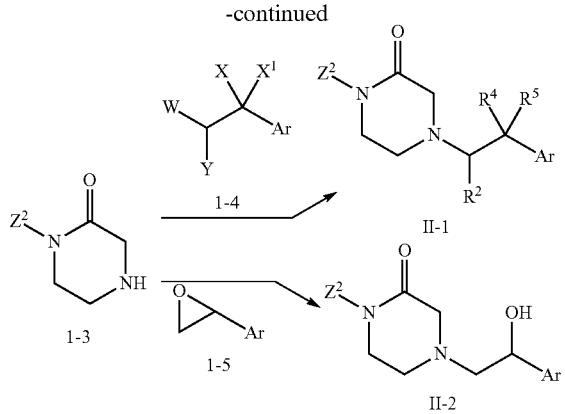

SCHEME 2

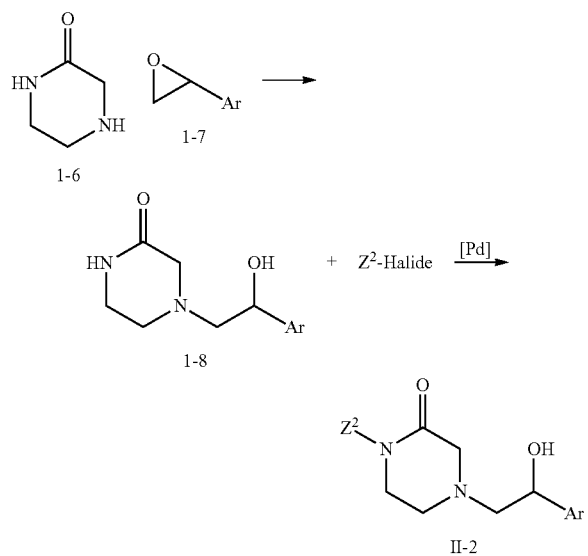

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry.

The subject compounds may be prepared by modification of the procedures disclosed in the Examples as appropriate. Starting materials are commercially available or made by known procedures or as illustrated. The following examples are provided for the purpose of further illustration only and are not intended to be limitations on the disclosed invention.

Reactions sensitive to moisture or air were performed under nitrogen or argon using anhydrous solvents and reagents. The progress of reactions was determined by either analytical thin layer chromatography (TLC) usually performed with E. Merck precoated TLC plates, silica gel 60E-254, layer thickness 0.25 mm or liquid chromatography-mass spectrometry (LC-MS; also referred to as "LC" in the experimental procedures herein). Typically the analytical LC-MS system used consisted of a Waters ZQ platform with electrospray ionization in positive ion detection mode with an Agilent 1100 series HPLC with autosampler. The column was usually a Water Xterra MS C18, 3.0×50 fexample 49 mm, 5 μm. The flow rate was 1 mL/min, and the injection volume was 10 μL. UV detection was in the range 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a Waters Chromatography Workstation configured with LC-MS System Consisting of: Waters ZQ single quad MS system with Electrospray Ionization, Waters 2525 Gradient Pump, Waters 2767 Injector/Collector, Waters 996 PDA Detetor, the MS Conditions of: 150-750 amu, Positive Electrospray, Collection Triggered by MS, and a Waters Sunfire C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 μL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by Biotage. Concentration of solutions was carried out on a rotary evaporator under reduced pressure. Flash chromatography was usually performed using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in $CDCl_3$ solutions unless otherwise noted. Chemical shifts were reported in parts per million (ppm). Tetramethylsilane (TMS) was used as internal reference in $CD_3Cl$ solutions, and residual $CH_3OH$ peak or TMS was used as internal reference in $CD_3OD$ solutions. Coupling constants (J) were reported in hertz (Hz). Chiral analytical chromatography was performed on one of Chiralpak AS, Chiralpak AD, Chiralcel OD, Chiralcel IA, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of Chiralpak AS, Chiralpak AD, Chiralcel OD, Ciralcel IA, or Chiralcel OJ columns (20×250 mm) (Daicel Chemical Industries, Ltd.) with desired isocratic solvent systems identified on chiral analytical chromatography or by supercritical fluid chromatography (SFC) conditions.

In the Examples, when a compound is obtained via chromatography (e.g., MPLC, HPLC, silica gel), it means that the solvent was removed (generally under vacuum) after the chromatography step to obtain the isolated product.

Abbreviations used herein include: —C(O)CH$_3$ (Ac); acetic acid (AcOH); —OC(O)CH$_3$ (OAc); aqueous (aq); Cbz (benzyloxycarbonyl); N,N-diisopropylethylamine (DIEA); N;N-dimethylformamide (DMF); ethyl acetate (EtOAc; EA); diethyl ether (ether or Et$_2$O); petroleum ether (Pet Ether; PE); 2-propanol (IPA); methyl t-butylether (MTBE); (benzotriazol-1-yloxy)tripyrrolidino-phosphonium hexafluorophosphate (PyBOP); saturated aq sodium chloride solution (brine); trifluoroacetic acid (TFA); tetrahydrofuran (THF); t-butyloxycarbonyl (Boc or BOC); Diethylaminosulfur trifluoride (DAST); dichloromethane (DCM); dimethylacetamide (DMA; DMAC); dimethylsulfoxide (DMSO); 1,3-Bis (diphenylphosphino)propane (DPPP); acetic acid (HOAc); 3-chloroperoxybenzoic acid (m-CPBA); methyl (Me);

methanol (MeOH); N-bromosuccinamide (NBS); N-methylmorpholine N-oxide (NMO); 1-hydroxybenzotriazole (HOBt); N-(3-dimethylaminopropyl)-N'-ethylcarbodiimide hydrochloride (EDC); diisopropyl azodicarboxylate (DIAD); lithium diisopropylamide (LDA); triethyl amine (TEA); di-tert-butydicarboxylate (BOC₂O); glycine methyl ester (GlyOMe); dimethyl sulfide (DMS); dichloroethane (DCE); N-iodosuccinamide (NIS); triflic acid or trifluoromethanesulfonic acid (TfOH); N-methyl morpholine (NMP); methanesulfonyl chloride (MsCl); 1,8-diazabicyclo[5.4.0]-undec-7-ene (DUB); p-toulenesulfonylmethyl isocyanide (TosMIC); dimethoxyethane (DME); tetramethyl ethylene diamine (TMEDA); 4-dimethylamino pyridine (DMAP); Pd₂ dba₃ (Tris(dibenzylideneacetone)dipalladium(0)); Xantphos (4,5-Bis(diphenylphosphino)-9,9-dimethylxanthene; gram(s) (g); milligram(s) (mg); microliter(s) (µL); milliliter(s) (mL); millimole (mmol); minute(s) (min, mins); hour(s) (h, hr or hrs); retention time (R$_t$); room temperature (rt, r.t. or RT); round bottom (RB); thin layer chromatography (TLC); flash chromatography (FC); liquid chromatography-mass spectrometry (LCMS or LC-MS); supercritical fluid chromatography (SFC); Medium Pressure Liquid Chromatography (MPLC); High Pressure Liquid Chromatography (HPLC); mass spectrum (ms or MS). Celite is the tradename for diatomaceous earth filter aid.

The following are representative procedures for the preparation of the compounds used in the following Examples, or which can be substituted for the compounds used in the following Examples which may not be commercially available.

INTERMEDIATE 1

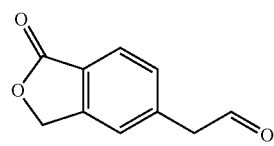

(1-Oxo-1,3-dihydro-2-benzofuran-5-yl)acetaldehyde

Step A: 5-(1,3-Dioxolan-2-ylmethyl)-2-benzofuran-1(3H)-one

A three-neck 5 L round bottomed flask equipped with a stir bar, firestone valve, thermocouple, condenser and heating mantle was charged with tri-t-butyl phosphonium tetrafluoroborate (500 mg, 1.72 mmol), palladium (II) acetate (250 mg, 1.1 mmol) and 5-bromo-2-benzofuran-1(3H)-one (100 g, 470 mmol). DMF (1.88 L) was added to the flask, and the mixture was degassed three times by alternating vacuum and nitrogen purge. Commercially available bromo(1,3-dioxolan-2-ylmethyl)zinc solution (1.03 L, 516 mmol) was added via canula and the mixture was again degassed three times. The mixture was then heated at 85° C. for 5 hours, checked by HPLC-MS, then stirred at 85° C. for 5 more hours. The mixture was then allowed to return to RT for overnight. 2-MethylTHF (2 L) and brine were added, and the mixture was stirred for 5 min. The layers were separated and the aqueous layer was extracted again with 2-methylTHF. The organic layers were combined, washed three times with brine (4 L each), dried over MgSO4, filtered and concentrated. The crude product was purified by flash chromatography (1.5 kg silica cartridge), eluting with 0-20% ethyl acetate in DCM to afford the title compound. LC-MS (IE, m/z): 221 [M+1]⁺.

Step B: (1-Oxo-1,3-dihydro-2-benzofuran-5-yl)acetaldehyde 5-(1,3-Dioxolan-2-ylmethyl)-2-benzofuran-1(3H)-one (61 g, 280 mmol) was combined with water (2.2 L) in a 5 L round bottomed flask equipped with a Claisen adapter, thermocouple, stir bar and nitrogen bubbler. Aqueous HCl solution (2M, 1.14 L, 2.29 mol) was added and the resulting mixture was heated at 40° C. for 8 h. Then the mixture was stirred overnight at room temperature. The mixture was extracted three times with 2 L of ethyl acetate. The combined organic layers were concentrated to give (1-oxo-1,3-dihydro-2-benzofuran-5-yl)acetaldehyde. LC-MS (IE, m/z): 177 (M+1)⁺.

INTERMEDIATE 2

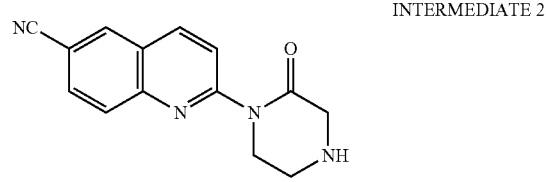 [SMILES: N#Cc1ccc2nc(N3CCNCC3=O)ccc2c1]

2-(2-Oxopiperazin-1-yl)quinoline-6-carbonitrile

Step A: 2-chloroquinoline-6-carbonitrile

To a flask containing a stir bar was added 6-bromo-2-chloroquinoline (0.90 g, 3.7 mmol), CuCN (0.50 g, 5.6 mmol) followed by addition of DMF (10 mL). The resulting mixture was then refluxed at 150° C. overnight. When the reaction appeared complete by LC analysis, the reaction flask was taken out of the oil bath and cooled to room temperature. To the reaction mixture was then poured DCM (20 mL) and a precipitate formed immediately, which was filtered, redissolved in DCM, absorbed onto silica gel, and purified by flash chromatography to provide the title product.

Step B: tert-Butyl 4-(6-cyanoquinolin-2-yl)-3-oxopiperazine-1-carboxylate

To a 25 mL flask was added a stir bar, 2-chloroquinoline-6-carbonitrile (0.015 g, 0.79 mmol), Pd₂ dba₃ (0.072 g, 0.08 mmol), Xantphos (0.09 g, 0.16 mmol), cesium carbonate (0.36 g, 1.13 mmol) and tert-Butyl 3-oxopiperazine-1-carboxylate (0.31 g, 1.6 mmol). The resulting mixture was degassed and purged with N₂ (3×). To the flask was added 1,4-dioxane (10 mL). The reaction mixture was then refluxed at 100° C. overnight. Analysis of the reaction mixture by LC indicated that reaction had gone to completion. The solution was concentrated in vacuo and the resulting crude was dissolved in EtOAc and washed with brine, dried over Na₂SO₄, filtered and concentrated in vacuo. The crude residue was purified by silica gel column chromatography (10% MeOH in DCM) to provide the title product.

Step C: 2-(2-Oxopiperazin-1-yl)quinoline-6-carbonitrile tert-Butyl 4-(6-cyanoquinolin-2-yl)-3-oxopiperazine-1-carboxylate (0.15 g, 0.79 mmol) was treated with TFA (2 mL) and stirred for 20 minutes. Analysis of the reaction mixture by LC indicated the reaction had gone to completion. The solution was concentrated in vacuo and crude was azetroped (3×) with dichloroethane to furnish the title product. LC/MS (IE, m/z): [M+1]$^+$=253.

INTERMEDIATE 3

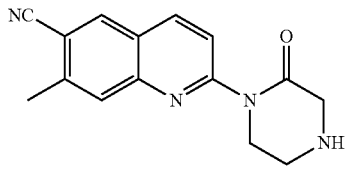

7-Methyl-2-(2-oxopiperazin-1-yl)quinoline-6-carbonitrile

Step A:
7-Methyl-2-oxo-1,2-dihydroquinoline-6-carbonitrile

A mixture of 6-bromo-7-methylquinolin (10 g, 42.0 mmol, prepared following J. Med. Chem. 1988, 31, 2048.), N-methyl-2-pyrrolidinone (32 mL), and CuCN (11 g, 0.13 mol) was stirred at 20° C. overnight and then at reflux temperature (202° C.) for 7 h. The mixture was poured into water (250 mL) and filtered, and the solid was washed twice with water to furnish 7-Methyl-2-oxo-1,2-dihydroquinoline-6-carbonitrile.

Step B: 2-Chloro-7-methylquinoline-6-carbonitrile

A mixture of 7-Methyl-2-oxo-1,2-dihydroquinoline-6-carbonitrile (10 g, 54 mmol) and POCl$_3$ (30 mL) was stirred at 110° C. for 2 h and then at 20° C. overnight. The mixture was carefully poured into a mixture of water and ice (400 mL) while being stirred vigorously. The product was collected by filtration and dried by co-evaporation with MeCN/Toluene to furnish the title product. LC/MS (IE, m/z): [M+1]$^+$=203.

Step C: tert-Butyl 4-(6-cyano-7-methylquinolin-2-yl)-3-oxopiperazine-1-carboxylate To a 25 mL flask was added a stir bar, 2-Chloro-7-methylquinoline-6-carbonitrile (0.2 g, 0.98 mmol), Pd$_2$ dba$_3$ (0.11 g, 0.19 mmol), Xantphos (0.090 g, 0.090 mmol), Cesium Carbonate (0.26 g, 0.63 mmol) and tert-Butyl 3-oxopiperazine-1-carboxylate (0.29 g, 1.4 mmol). The resulting mixture was degassed and purged with N$_2$ three times. To the flask was added 1,4-dioxane (4 mL). The reaction mixture was then refluxed at 100° C. overnight. The solution was concentrated in vacuo and the resulting crude was dissolved in EtOAc and washed with brine, dried over Na$_2$SO$_4$, filtered and concentrated in vacuo. The crude residue was then purified by silica gel column chromatography (10% MeOH in DCM) to provide the title compound.

Step D: 7-Methyl-2-(2-oxopiperazin-1-yl)quinoline-6-carbonitrile tert-Butyl 4-(6-cyano-7-methylquinolin-2-yl)-3-oxopiperazine-1-carboxylate was treated with TFA (2 mL) and stirred for 20 minutes. Analysis of the reaction mixture by LC indicated that reaction had gone to completion. The solution was concentrated in vacuo and crude was azetroped (3×) with dichloroethane to furnish the title compound. LC/MS (IE, m/z): [M+1]$^+$=267.

INTERMEDIATE 4

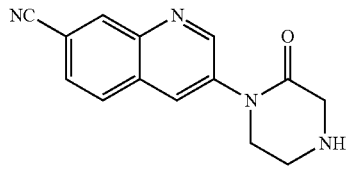

3-(2-Oxopiperazin-1-yl)quinoline-7-carbonitrile

Step A: 3-Chloroquinoline-7-carbonitrile

To a flask containing a stir bar was added 7-Bromo-3-chloroquinoline (1.0 g, 4.1 mmol), CuCN (0.55 g, 6.2 mmol), and DMF (25 mL). The mixture was then refluxed at 150° C. overnight. When the reaction was complete, as evidenced by LC analysis, the reaction flask was taken out of the oil bath and cooled to room temperature. To the reaction mixture was then poured DCM (20 mL) and a precipitate formed immediately, which was filtered off. The crude product was adsorbed onto silica gel and purified by silica gel column chromatography (Hexanes:DCM→1:1) to provide the title product.

Step B: tert-Butyl 4-(7-cyanoquinolin-3-yl)-3-oxopiperazine-1-carboxylate

To a 25 mL flask was added a stir bar, 7-Chloroquinoline-3-carbonitrile (0.36 g, 1.9 mmol), Pd$_2$ dba$_3$ (0.17 g, 0.19 mmol), Xantphos (0.22 g, 0.38 mmol), cesium carbonate (0.70 g, 2.3 mmol) and tert-butyl 3-oxopiperazine-1-carboxylate (0.45 g, 2.3 mmol). The resulting mixture was degassed and purged with N$_2$ (3×). To the flask was added 1,4-dioxane (0.75 mL). The reaction mixture was then heated to 100° C. overnight. The solution was concentrated in vacuo and the resulting crude was dissolved in EtOAc and washed with brine, dried over Na$_2$SO$_4$, filtered and concentrated in vacuo. The crude residue was then purified by silica gel column chromatography (5% MeOH in DCM) to provide the title product.

Step C: 3-(2-Oxopiperazin-1-yl)quinoline-7-carbonitrile tert-Butyl 4-(7-cyanoquinolin-3-yl)-3-oxopiperazine-1-carboxylate (0.030 g, 0.099 mmol) was treated with TFA (2 mL) and stirred for 20 minutes. Analysis of the reaction mixture by LC indicated that reaction had gone to completion. The solution was concentrated in vacuo and crude was azetroped with dichloroethane (3×8 mL) to furnish the title product. LC/MS (IE, m/z): [M+1]$^+$=253.

INTERMEDIATE 5

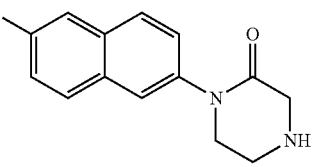

6-(2-Oxopiperazin-1-yl)naphthalene-2-carbonitrile hydrochloride

Step A: tert-Butyl 4-(6-bromo-2-naphthyl)-3-oxopiperazine-1-carboxylate

To a microwave tube charged with a stir bar was added 2,6-dibromonaphthalene (710 mg, 2.5 mmol), tert-butyl 3-oxopiperazine-1-carboxylate (250 mg, 1.2 mmol), copper (I) iodide (48 mg, 0.25 mmol), N,N'-dimethylcyclohexane-1,2-diamine (71 mg, 0.50 mmol), $K_3PO_4$ (530 mg, 2.5 mmol), and dioxane (10 mL). The mixture was heated to 150° C. in a microwave reactor for 1 hour. The reaction was diluted with EtOAc, adsorbed onto silica gel, and purified by MPLC (silica gel, EtOAc-Hexanes) to afford the title compound. LC-MS (IE, m/z): 407 [M+1]+.

Step B: 6-(2-Oxopiperazin-1-yl)naphthalene-2-carbonitrile hydrochloride

To a flask charged with tert-butyl 4-(6-bromo-2-naphthyl)-3-oxopiperazine-1-carboxylate (500 mg, 1.2 mmol) and a stir bar was added copper(I) cyanide (220 mg, 2.5 mmol) and DMF (20 mL). The mixture was heated to 135° C. for 12 hours under an atmosphere of $N_2$. The reaction was diluted with EtOAc, washed with sat. $NH_4OAc$ and brine, dried over sodium sulfate, concentrated and purified by silica gel chromatography. The resulting product was treated with 4N HCl in dioxane, and removal of solvent furnished the title compound. LC-MS (IE, m/z): 252 [M+1]+. The salt was further washed with aqueous sodium carbonate, and back extracted with $CHCl_3$-IPA (3:1).

INTERMEDIATE 6

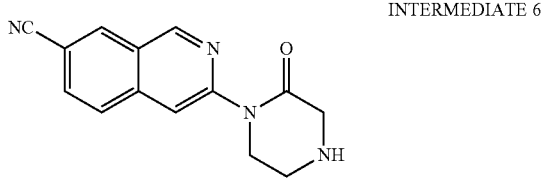 [SMILES: N#Cc1ccc2cc(N3CCNCC3=O)ncc2c1]

3-(2-oxopiperazin-1-yl)isoquinoline-7-carbonitrile

Step A: 3-Chloroisoquinoline-7-carbonitrile

To a flask charged with 7-bromo-3-chloroisoquinoline (1.0 g, 4.1 mmol) and a stir bar was added copper(I) cyanide (550 mg, 6.2 mmol) and DMF (50 mL). The mixture was heated to 150° C. for 24 hours under an atmosphere of nitrogen. The reaction was diluted with EtOAc, washed with sat. $NH_4OAc$ and brine, dried over sodium sulfate, concentrated and purified by silica gel chromatography (Hexanes:DCM) and the solvent removed to afford the title compound. LC-MS (IE, m/z): 189 [M+1]+.

Step B: 3-(2-oxopiperazin-1-yl)isoquinoline-7-carbonitrile hydrochloride

To a flask charged with 3-chloroisoquinoline-7-carbonitrile (250 mg, 1.3 mmol) and a stir bar was added tert-butyl 3-oxopiperazine-1-carboxylate (400 mg, 2.0 mmol), $Pd_2(dba)_3$ (120 mg, 0.13 mmol), Xantphos (150 mg, 0.26 mmol), cesium carbonate (650 mg, 2.0 mmol), and dioxane (20 mL). The mixture was purged three times with nitrogen, and heated to 100° C. for 16 hours. The mixture was diluted with EtOAc, washed with brine, dried over sodium sulfate, adsorbed onto silica gel, and purified by silica gel chromatography (Hexanes:EtOAc) to provide tert-butyl 4-(7-cyanoisoquinolin-3-yl)-3-oxopiperazine-1-carboxylate. LC-MS (IE, m/z): 353 [M+1]+.

Step C: 3-(2-oxopiperazin-1-yl)isoquinoline-7-carbonitrile

The product of Step B was further treated with 4N HCl in dioxane, and removal of solvent furnished 3-(2-oxopiperazin-1-yl)isoquinoline-7-carbonitrile hydrochloride. The HCl salt was washed with aqueous sodium carbonate, and back extracted with $CHCl_3$-IPA (3:1) to furnish the title compound.

INTERMEDIATE 7

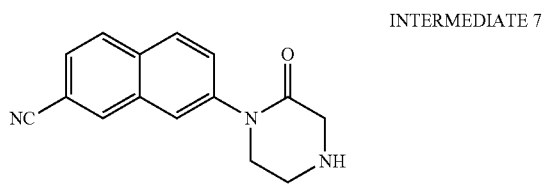 [SMILES: N#Cc1ccc2ccc(N3CCNCC3=O)cc2c1]

7-(2-oxopiperazin-1-yl)naphthalene-2-carbonitrile

Step A: tert-Butyl 4-(7-bromo-2-naphthyl)-3-oxopiperazine-1-carboxylate

To a 20 mL microwave vial charged with 2,7-dibromonaphthalene (1.1 g, 3.8 mmol), tert-butyl 3-oxopiperazine-1-carboxylate (0.50 g, 2.5 mmol), and a stir bar was added copper (I) iodide (95 mg, 0.50 mmol), N,N'-dimethylcyclohexane-1,2-diamine (142 mg, 1.0 mmol), $K_3PO_4$ (1100 mg, 5.0 mmol), and dioxane (15 mL). The mixture was purged three times with nitrogen, and heated to 150° C. in a microwave reactor. The crude solution was diluted with EtOAc, adsorbed onto silica gel, and purified by silica gel chromatography (Hex:EtOAc). The solvent was removed to provide the title compound. LC-MS (IE, m/z): 405 [M+1]+.

Step B: 7-(2-oxopiperazin-1-yl)naphthalene-2-carbonitrile

To a flask charged with tert-Butyl 4-(7-bromo-2-naphthyl)-3-oxopiperazine-1-carboxylate (450 mg, 1.1 mmol) and a stir bar was added copper (I) cyanide (300 mg, 3.3 mmol) and DMF (10 mL). The mixture was heated to 140° C. for 16 hours. The reaction was diluted with DCM. The solids were filtered off. The filtrate was concentrated, adsorbed onto silica gel, and purified by silica gel chromatography (Hex:EtOAc 1:1) to afford tert-butyl 4-(7-bromo-2-naphthyl)-3-oxopiperazine-1-carboxylate. LC-MS (IE, m/z): 352 [M+1]+. The product was further treated with TFA to remove the Boc group. The resulting TFA salt was washed with aqueous sodium carbonate, and back extracted with $CHCl_3$-IPA (3:1) to furnish the title compound.

INTERMEDIATE 8

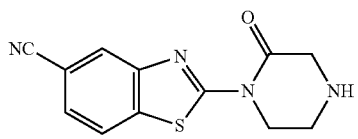

2-(2-oxopiperazin-1-yl)-1,3-benzothiazole-5-carbonitrile

To a flask charged with 2-chloro-1,3-benzothiazole-5-carbonitrile [prepared from 3-amino-4-chlorobenzonitrile following the procedure described in US Publication 2009/0197862, Example 267] (146 mg, 0.75 mmol) and a stir bar was added tert-butyl 3-oxopiperazine-1-carboxylate (225 mg, 1.1 mmol), $Pd_2(dba)_3$ (69 mg, 0.075 mmol), Xantphos (87 mg, 0.15 mmol), cesium carbonate (370 mg, 1.1 mmol), and dioxane (10 mL). The mixture was purged three times with nitrogen, and heated to 100° C. under $N_2$ for 16 hours. The reaction was diluted with EtOAc, adsorbed onto silica gel, and purified by silica gel chromatography (Hexanes: EtOAc 1:1) to provide tert-butyl 4-(5-cyano-1,3-benzothiazol-2-yl)-3-oxopiperazine-1-carboxylate (95 mg, 35% yield). The carboxylate was further treated with TFA to remove the Boc group. After removal of TFA, the residue was dissolved in aqueous sodium carbonate, extracted with DCM, dried over sodium sulfate, and concentrated to provide the free base of 2-(2-oxopiperazin-1-yl)-1,3-benzothiazole-5-carbonitrile. LC-MS (IE, m/z): 259 [M+1]$^+$.

INTERMEDIATE 9

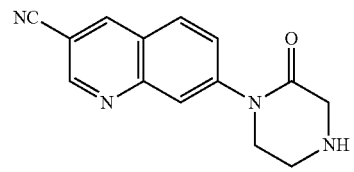

7-(2-oxopiperazin-1-yl)quinoline-3-carbonitrile

Step A: 7-chloroquinoline-3-carbonitrile

To a flask containing a stir bar was added 3-bromo-7-chloroquinoline (1.0 g, 4.1 mmol), CuCN (0.55 g, 6.2 mmol) followed by addition of DMF (25 mL). The resulting mixture was then heated to 150° C. overnight. When the reaction was complete as evidenced by LC analyisis, the reaction flask was taken out of the oil bath and cooled to RT. To the reaction mixture was then poured DCM (20 mL) and a precipitate formed immediately, which was filtered. The filtrated was washed with aq. $NH_4Cl$, dried over sodium sulfate, and purified by flash chromatography. LC-MS (IE, m/z): 189 [M+1]$^+$.

Step B: tert-butyl 4-(3-cyanoquinolin-7-yl)-3-oxopiperazine-1-carboxylate

To a 25 mL flask was added a stir bar, 7-chloroquinoline-3-carbonitrile (0.15 g, 0.79 mmol), $Pd_2 dba_3$ (0.072 g, 0.08 mmol), Xantphos (0.090 g, 0.16 mmol), cesium carbonate (0.36 g, 1.13 mmol) and tert-butyl 3-oxopiperazine-1-carboxylate (0.31 g, 1.6 mmol). The resulting mixture was degassed and purged with $N_2$ (3x). To the flask was added 1,4 dioxane (10 mL). The resulting reaction mixture was then refluxed at 100° C. for overnight. Analysis of the reaction mixture by LC indicated that reaction had gone to completion. The solution was concentrated in vacuo and the resulting crude was dissolved in EtOAc and washed with brine, then dried over $Na_2SO_4$, filtered and concentrated in vacuo. The crude residue was then subjected for purification by silica gel column chromatography (10% MeOH in DCM) to provide the title product.

Step C: 7-(2-oxopiperazin-1-yl)quinoline-3-carbonitrile tert-Butyl 4-(3-cyanoquinolin-7-yl)-3-oxopiperazine-1-carboxylate was treated with TFA (2 mL) for 20 minutes at RT. The TFA was removed under vacuum, and the residue was dissolved in aqueous sodium carbonate, extracted with DCM, dried over sodium sulfate, and concentrated to deliver the free base of 7-(2-oxopiperazin-1-yl)quinoline-3-carbonitrile. LC-MS (IE, m/z): 253 [M+1]$^+$.

INTERMEDIATE 10

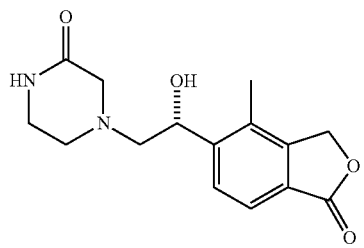

4-[(2R)-2-Hydroxy-2-(4-methyl-1-oxo-1,3-dihydro-2-benzofuran-5-yl)ethyl]piperazin-2-one A mixture of 4-Methyl-5-[(2R)-oxiran-2-yl]-2-benzofuran-1(3H)-one (0.46 g, 2.4 mmol) and piperazin-2-one (0.20 g, 2.0 mmol) was heated to 145° C. in a microwave tube for 1 hour. The crude reaction was diluted with DCM, adsorbed onto silica gel, and purified by silica gel chromatography to provide the title product. LC-MS (IE, m/z): 291 (M+1)$^+$.

INTERMEDIATE 11

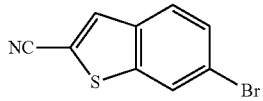

6-Bromo-1-benzothiophene-2-carbonitrile

A mixture of 6-bromo-1-benzothiophene-2-carboxylic acid (prepared in a similar manner to J. Med. Chem. (2007), 50(20), 4793-4807) (240 mg, 0.95 mmol) and thionyl chloride was heated to 75° C. in 10 mL of DCE until the mixture becomes homogeneous, about 1 hour. The reaction was then concentrated to dryness and redissolved in 10 mL of DCE and then excess 2N ammonia in MeOH was added (about 10 mL) and the reaction stirred at room temp for 30 minutes before excess solvent was removed. The crude amide was then redissolved in DCM, the salts were filtered off and the filtrate concentrated. The crude amide was then taken up in phosphorus oxychloride (10 mL) and heated at 80° C. for 2 hours and then cooled to RT. The reaction was partitioned between DCM and water, the organic layer was then washed with brine, dried over magnesium sulfate, filtered and purified via MPLC (0-10% EtOAc/Hex) to give 6-Bromo-1-benzothiophene-2-carbonitrile. $^1$H NMR (500 MHz; CDCl$_3$): 8.06 (d, J=1.4 Hz, 1H), 7.88 (s, 1H), 7.78 (d, J=8.6 Hz, 1H), 7.62 (dd, J=1.4, 8.6 Hz, 1H). LC-MS (IE, m/z): 238 [M+1]$^+$.

INTERMEDIATE 12

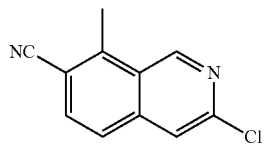

3-Chloro-8-methylisoquinoline-7-carbonitrile

Step A: 7-bromo-3-chloro-8-iodoisoquinoline

To a flask containing 7-Bromo-3-chloroisoquinoline (1.5 g, 6.19 mmol) was added NIS (1.4 g, 6.9 mmol). The flask was placed in an ice bath and treated with TfOH (40 mL) and stirred at RT overnight. The reaction mixture was carefully poured into ice, and the aqueous layer was extracted with DCM. The combined extracts were washed with brine, dried over Na$_2$SO$_4$, and concentrated under reduced pressure. The crude residue was purified by silica gel column chromatography (Hexanes:DCM→1:1) to provide the title product.

Step B: 7-Bromo-3-chloro-8-methylisoquinoline

To a 20 mL microwave tube was added a stir bar, 7-bromo-3-chloro-8-methylisoquinoline (0.81 g, 2.2 mmol), Pd$_2$ dba$_3$ (0.20 g, 0.22 mmol) and triphenylphosphine (0.12 g, 0.44 mmol). The tube was capped, degassed and then purged with N$_2$ and heated in a microwave reactor at 50° C. for 10 minutes. The cap was removed, and the tube treated with copper (I) iodide (0.04 g, 0.22 mmol), capped, degassed and purged with N$_2$ and heated again 50° C. for 10 minutes. The cap was once again opened and to the tube was added tetramethyltin (0.30 mL, 2.4 mmol), which was followed by capping, degassing and purging of the reaction mixture with N$_2$, and heating it to 120° C. for 30 minutes. To the mixture was added water, and the aqueous layer was extracted with DCM. The combined extracts were washed with brine, dried over Na$_2$SO$_4$, and concentrated under reduced pressure. The crude residue was purified by silica gel column chromatography (Hexanes: DCM→1:1) to provide the title product. LC/MS (IE, m/z): [M+1]$^+$=257.

Step C: 3-Chloro-8-methylisoquinoline-7-carbonitrile

To a flask containing a stir bar was added 7-Bromo-3-chloro-8-methylisoquinoline (0.63 g, 2.4 mmol), CuCN (0.33 g, 3.7 mmol), and DMF (10 mL). The mixture was then refluxed at 150° C. overnight. When the reaction was complete, as evidenced by LC analysis, the reaction flask was taken out of the oil bath and cooled to room temperature. To the mixture was then poured DCM (20 mL) and a precipitate formed immediately, which was filtered, re-dissolved in DCM, adsorbed into silica gel and purified by silica gel column chromatography (Hexanes:DCM→1:1) to provide the title product. LC/MS (IE, m/z): [M+1]$^+$=203.

INTERMEDIATE 13

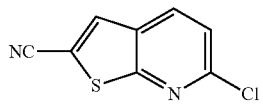

6-Chlorothieno[2,3-b]pyridine-2-carbonitrile

Step A: 6-Chloro-2-iodothieno[2,3-b]pyridine

To a flask charged with 6-Chlorothieno[2,3-b]pyridine (500 mg, 3.0 mmol) and a stir bar was added NIS (800 mg, 3.5 mmol) and Triflic acid (5 mL). The mixture was monitored by TLC and allowed to stir at RT for 4 hours. The reaction was poured into ice, neutralized with aqueous sodium carbonate, extracted with DCM, dried over sodium sulfate, concentrated and purified by flash chromatography (Hex: EtOAc gradient) to obtain the title product. LC-MS (IE, m/z): 296 [M+1]$^+$.

Step B: 6-Chlorothieno[2,3-b]pyridine-2-carbonitrile

A mixture of 6-Chloro-2-iodothieno[2,3-b]pyridine (80 mg, 0.27 mmol) and Copper (I) Cyanide (36 mg, 0.41 mmol) in DMF (3 mL) was heated to 130° C. for 16 hrs. LC showed formation of the title product. The crude reaction was adsorbed onto silica gel, and purified by flash chromatography to obtain the title product. LC-MS (IE, m/z): 195 [M+1]$^+$.

INTERMEDIATE 14

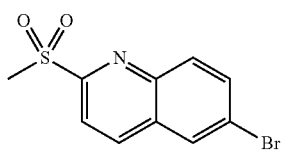

6-Bromo-2-(methylsulfonyl)quinoline

Step A: 6-Bromo-2-(methylsulfanyl)quinoline

A solution of 6-Bromo-2-chloroquinoline (0.68 g, 2.8 mmol) in DMF was treated with sodium thiomethoxide (0.22 g, 3.1 mmol). After 1 h at RT, the LC-MS indicated conversion. The solution was diluted with brine and extracted with EtOAc. The organic layer was removed, dried, filtered and concentrated. The crude product was used in the next step. LC-MS (IE, m/z): 256 [M+1]$^+$.

Step B: 6-Bromo-2-(methylsulfonyl)quinoline

A stirred solution of 6-Bromo-2-(methylsulfanyl)quinoline in DCM was treated with m-CPBA (1.07 g, 6.2 mmol) at RT. After 1 hour, TLC and LC-MS indicated conversion. The solvent was removed and the material was dissolved in minimal DCM and purifed via MPLC. The title compound eluted with 0-60% EtOAc, and the solvent was removed to obtain the title product. LC-MS (IE, m/z): 288 [M+1]$^+$.

INTERMEDIATE 15A and 15B

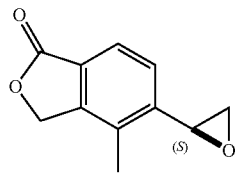

I-15a

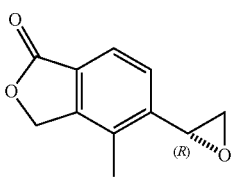

I-15B

I-15A: 4-Methyl-5-[(2R)-oxiran-2-yl]-2-benzofuran-1(3H)-one and

I-15B: 4-Methyl-5-[(2S)-oxiran-2-yl]-2-benzofuran-1(3H)-one

Step A: (3-Bromo-2-methylphenyl)methanol

To a solution of 3-bromo-2-methyl benzoic acid (35 g, 163 mmol) in THF (200 mL) was added Borane THF Complex (1.0 M, 212 mL, 212 mmol). The mixture was allowed to stir for 24 h. The reaction was then quenched with water. The THF was removed under reduced pressure. The resulting solid was dissolved in ethyl acetate (500 mL), washed with 1N HCl, sodium carbonate, and brine. The organic layer was dried over sodium sulfate and concentrated to afford (3-bromo-2-methylphenyl)methanol.

Step B: 5-Bromo-4-methyl-2-benzofuran-1(3H)-one

To a flask charged with (3-bromo-2-methylphenyl)methanol (6.0 g, 30 mmol) was added a 1M TFA solution of Thallium Trifluoroacetate (16.2 g, 29.8 mmol). The mixture was stirred at RT overnight. The solvent was removed under vacuum, and the residue was pumped under high vacuum for 30 min to ensure complete removal of TFA. To the residue was then added palladium(II) chloride (529 mg, 2.98 mmol), lithium chloride (2.53 g, 59.7 mmol), magnesium oxide (2.41 g, 59.7 mmol), and MeOH (150 mL). The reaction was flushed with CO twice, and kept under CO at RT. Analysis by LC showed a formation of product within 2 hours. To this solution was added ethyl acetate to precipitate the salts. The solution was filtered through a celite pad, washed with EtOAc, adsorbed onto silica and purified by silica gel chromatography to provide the title compound Step C: 5-ethenyl-4-methyl-2-benzofuran-1(3H)-one 5-Bromo-4-methyl-2-benzofuran-1(3H)-one (598 mg, 4.47 mmol), potassium vinyl trifluoroborate (507 mg, 2.23 mmol), $PdCl_2(dppf)-CH_2Cl_2$ Adduct (182 mg, 0.223 mmol), and TEA (0.622 mL, 4.47 mmol) were added to 10 mL ethanol in a 20 mL microwave tube. The tube was sealed and degassed, then heated to 140° C. for 20 min. Analysis by LC-MS showed product peak. The reaction mixture was diluted with ethyl acetate, washed with brine twice, dried and evaporated to dryness. The crude product was purified by MPLC chromatography using a 120 g Redi-sep column and 0-80% EtOAC/Hexane solvent system to yield the title product. LC-MS: M+1=175 at 2.42 retention time.

Step D: 4-methyl-5-oxiran-2-yl-2-benzofuran-1(3H)-one 5-ethenyl-4-methyl-2-benzofuran-1(3H)-one (1.46 g, 8.38 mmol) was added to DCM (25 mL) at 0° C. then m-CPBA (2.89 g, 16.8 mmol) was added and the mixture was stirred at RT overnight. The reaction mixture was washed once each with saturated aqueous $Na_2S_2O_3$, $NaHCO_3$, and brine. The organic layer was dried over $Na_2SO_4$, filtered, and evaporated to dryness. The crude material was purified by MPLC chromatography through 120 g Redi-sep column eluting with 0-80% EtOAc/hexane solvent system to yield 4-methyl-5-oxiran-2-yl-2-benzofuran-1(3H)-one. $^1$H-NMR (500 MHz, $CDCl_3$): δ ppm 7.77 (d, J=8 Hz, 1H), 7.43 (d, J=8 Hz, 1H), 5.30 (s, 2H), 4.12 (s, 1H), 3.27 (t, J=4 Hz, 1H), 2.735 (dd, J=2.2, 5.5 Hz, 1H), 2.43 (s, 3H).

Step E: I-15A (Slower Eluting Isomer) and I-15B (Faster Eluting Isomer)

Racemic 4-methyl-5-oxiran-2-yl-2-benzofuran-1(3H)-one was resolved on a ChiralPak® AD-H column (5×25 cm) under SFC conditions on a Berger MGIII preparative SFC instrument. The racemate was diluted to 50 mg/ml in 1:1 DCM:MeOH. The separation was accomplished using 10% EtOH/$CO_2$, flow rate 200 ml/min, 100 bar, 25° C. 500 ul Injections were spaced every 2.12 mins. The faster eluting (2R)-epoxide (I-15B) eluted at 5.2 min, and the slower eluting (2S)-epoxide (I-15A) eluted at 5.6 min.

INTERMEDIATE 16

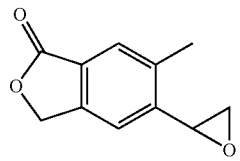

6-Methyl-5-(oxiran-2-yl)-2-benzofuran-1(3H)-one

Step A: 5-Prop-2-en-1-yl-2-benzofuran-1(3H)-one

A mixture of 5-bromo-2-benzofuran-1(3H)-one (15.0 g, 70.4 mmol), allyl-tributyl-stannane (25.6 g, 77.5 mmol), LiCl (11.8 g, 282 mmol) and $Pd(PPh_3)_4$ (1.2 g, 1.0 mmol) in 100 mL toluene was heated under $N_2$ at 90~100° C. overnight. After cooling to RT, the mixture was diluted with 250 mL EtOAc and filtered. The filtrate was washed with water and brine, dried over anhydrous $Na_2SO_4$ and concentrated to dryness. The residue was purified via column (DCM/Pet Ether=1:5) to give the title compound.

Step B: 5-(2-hydroxyethyl)-2-benzofuran-1(3H)-one

To a solution of 5-prop-2-en-1-yl-2-benzofuran-1(3H)-one (13.5 g, 45.2 mmol) in 200 mL DCM/MeOH (V/V=1:1) was bubbled $O_3$ at −78° C. for 30 min, and $N_2$ was bubbled for another 15 min at −78° C. Then 20 mL of $Me_2S$ were added, and the mixture was stirred at RT overnight before concentrating to dryness. The residue was dissolved in MeOH (100 mL) and then cooled to 0° C. $NaBH_4$ (5.90 g, 155 mmol) was added in portions. The resulting mixture was stirred at 0° C. for 1 h, then quenched with citric acid (aq.) and extracted three times with EtOAc. The combined organic layers were washed with $NaHCO_3$ (aq.) and brine, dried over anhydrous $Na_2SO_4$ and concentrated to dryness. The residue was purified via column chromatography (EtOAc/Pet Ether=1:5) to give 5-(2-hydroxyethyl)-2-benzofuran-1(3H)-one.

Step C: 5-(2-hydroxyethyl)-6-iodo-2-benzofuran-1(3H)-one

To a cooled (0° C.) solution of 5-(2-hydroxyethyl)-2-benzofuran-1(3H)-one (9.00 g, 50.6 mmol) in 100 mL of TfOH was added NIS (12.5 g, 55.6 mmol), then the mixture was stirred at 0° C. for 2 hrs and then poured into ice-water (500 mL). The solution was extracted three times with 500 mL of EtOAc and the combined organic layers were washed with saturated NaHCO$_3$ and brine, dried over anhydrous sodium sulfate, filtered and concentrated. The residue was purified by column chromatography (EtOAc/Pet Ether=1:5) to give the title compound.

Step D: 5-(2-hydroxyethyl)-6-methyl-2-benzofuran-1(3H)-one

To a flask charged with 5-(2-hydroxyethyl)-6-iodo-2-benzofuran-1(3H)-one (6.00 g, 19.7 mmol) and a stir bar was added Pd$_2$(dba)$_3$ (452 mg, 0.493 mmol), PPh$_3$ (1 g, 4 mmol) and NMP (50 mL). The mixture was purged with N$_2$ and heated to 50° C. for 10 min, followed by addition of CuI (375 mg, 1.97 mmol). After the mixture was heated for another 10 min, Sn(CH$_3$)$_4$ (5.30 g, 29.6 mmol) was added into the reaction, and it was heated to 120° C. for 2 h. After cooling to RT, the mixture was diluted with saturated NH$_4$Cl (200 mL) and extracted with EtOAc (3×200 mL). The combined organic layers were washed with water and brine, dried over anhydrous sodium sulfate, filtered and concentrated. The residue was purified by prep-HPLC to give the title compound.

Step E: 2-(6-methyl-1-oxo-1,3-dihydro-2-benzofuran-5-yl)ethyl methanesulfonate To a solution of 5-(2-hydroxyethyl)-6-methyl-2-benzofuran-1(3H)-one (1.20 g, 6.25 mmol) and TEA (2.5 g, 25 mmol) in DCM (100 mL) was added MsCl (1.40 g, 12.5 mmol) at 0° C. The mixture was stirred at ambient temperature overnight, then was washed with water and brine. The organic layer was dried and concentrated to dryness to obtain the title compound.

Step F: 5-ethenyl-6-methyl-2-benzofuran-1(3H)-one

To a mixture of 2-(6-methyl-1-oxo-1,3-dihydro-2-benzofuran-5-yl)ethyl methanesulfonate (2.00 g, 7.41 mmol) and TEA (5 mL) in DCM (50 mL) was added DBU (5 mL) slowly at 0° C. The mixture was stirred at r.t. overnight, and then was diluted with 50 mL of DCM, washed with 2 N HCl three times and brine. The organic layer was dried and concentrated to dryness. The residue was purified by prep-TLC to give 5-ethenyl-6-methyl-2-benzofuran-1(3H)-one.

Step G: 6-methyl-5-oxiran-2-yl-2-benzofuran-1(3H)-one

To a solution of 5-ethenyl-6-methyl-2-benzofuran-1(3H)-one (1.00 g, 5.75 mmol) in 50 mL of DCM was slowly added m-CPBA (3.50 g, 17.4 mmol) in 50 mL of DCM at 0° C. The mixture was warmed to room temperature, and stirred for 2 days. The mixture was washed with aqueous Na$_2$SO$_3$ until KI indicator paper didn't change color. The organic layer was washed with brine and then concentrated. The residue was purified via silica column to give product 6-methyl-5-oxiran-2-yl-2-benzofuran-1(3H)-one. LC/MS (IE, m/z): [M+1]$^+$=191.

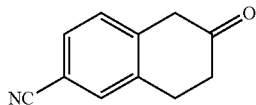

INTERMEDIATE 17

6-Oxo-5,6,7,8-tetrahydronaphthalene-2-carbonitrile

To a 20 mL microwave tube was added 5-bromo-2-tetralone (2.0 g, 8.9 mmol) and Palladium(0) Tetrakis (0.616 g, 0.533 mmol), zinc cyanide (1.0 g, 8.9 mmol), and DMF (8 mL). The tube was sealed, degassed and microwaved at 80° C. for 1.0 hour. TLC showed no starting material left. The mixture was diluted with ethyl acetate, washed with ammonium hydroxide (2M, 2×), dried with sodium sulfate, filtered and evaporated under reduced pressure. The product was purified by silica gel chromatography with isocratic 30% ethyl acetate-hexane to furnish the title compound. $^1$H-NMR (500 MHz, CDCl$_3$) δ ppm 7.57 (s, 1H), 7.55 (d, J=7.8 Hz, 1H), 7.28 (d, J=7.8 Hz, 1H), 3.67 (s, 2H), 3.14 (t, J=7.0 Hz, 2H), 2.60 (t, J=7.0 Hz, 2H).

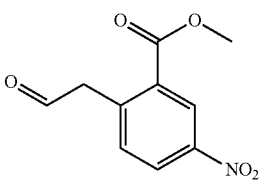

INTERMEDIATE 18

Methyl 5-nitro-2-(2-oxoethyl)benzoate

Step A: Methyl 5-nitro-2-(prop-2-en-1-yl)benzoate

A mixture of Methyl 2-bromo-5-nitrobenzoate (0.60 g, 2.3 mmol), allyl tri-n-butyltin (0.92 g, 2.8 mmol), lithium chloride (0.29 g, 6.9 mmol), and palladium tetrakis (0.13 g, 0.12 mmol) was heated to reflux for 16 hours in toluene. TLC showed formation of the desired product. The reaction was diluted with EtOAc, washed with brine, and separated. The organic layer was dried over sodium sulfate, filtered and concentrated under reduced pressure. The residue was purified by silica gel chromatography to obtain the title compound.

Step B: Methyl 5-nitro-2-(2-oxoethyl)benzoate

To a solution of Methyl 5-nitro-2-(prop-2-en-1-yl)benzoate (0.20 g, 0.90 mmol) in water (2 mL) and THF (5 mL) was added osmium tetroxide (0.57 mL 2.5% solution, 0.045 mmol) and NMO (0.16 g, 1.4 mmol). The mixture was allowed to stir at RT for 16 hours and monitored by TLC. The reaction was diluted with EtOAc, washed with NH$_4$Cl and brine, and concentrated. The residue was redissolved in MeOH and water. After cooling the solution to 0° C., an aqueous solution of sodium periodate (0.39 g, 1.8 mmol) was dropped into the reaction and allowed to stir for 2 hours. The reaction was diluted with water, extracted with EtOAc, dried over sodium sulfate, and concentrated. The crude residue was purified by silica gel chromatography to provide Methyl 5-nitro-2-(2-oxoethyl)benzoate. $^1$H-NMR (400 MHz, CDCl$_3$) δ ppm 9.48 (S, 1H), 8.97 (s, 1H), 8.39 (d, J=8.0 Hz, 1H), 7.46 (d, J=8.0 Hz, 1H), 4.31 (s, 2H), 3.98 (s, 3H).

INTERMEDIATE 19

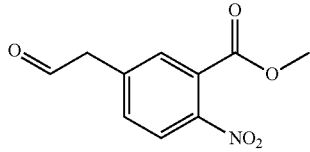

Methyl 2-nitro-5-(2-oxoethyl)benzoate

The title compound was prepared from Methyl 5-chloro-2-nitrobenzoate using essentially the same procedure as described for Intermediate 40. $^1$H-NMR (400 MHz, CDCl$_3$) δ ppm 9.84 (S, 1H), 7.98 (d, J=8.0 Hz, 1H), 7.61 (s, 1H), 7.50 (d, J=8.0 Hz, 1H), 3.98 (s, 3H), 3.94 (s, 2H).

INTERMEDIATE 20

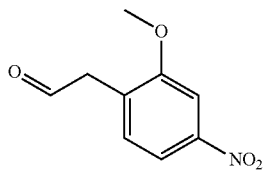

(2-Methoxy-4-nitrophenyl)acetaldehyde

The title compound was prepared from 1-Bromo-2-methoxy-4-nitrobenzene using essentially the same procedure as described for Intermediate 40. $^1$H-NMR (500 MHz, CDCl$_3$) δ ppm 9.78 (S, 1H), 7.89 (d, J=8.0 Hz, 1H), 7.78 (s, 1H), 7.35 (d, J=8.0 Hz, 1H), 3.98 (s, 3H), 3.81 (s, 2H).

INTERMEDIATE 21

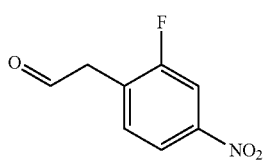

(2-Fluoro-4-nitrophenyl)acetaldehyde

The title compound was prepared from 1-Bromo-2-fluoro-4- using essentially the same procedure as described for Intermediate 40. $^1$H-NMR (500 MHz, CDCl$_3$) δ ppm 9.86 (S, 1H), 8.10 (m, 1H), 8.01 (m, 1H), 7.43 (m, 1H), 3.97 (s, 2H).

INTERMEDIATE 22

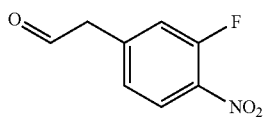

3-Fluoro-4-nitrophenylacetaldehyde

The title compound was prepared from 4-Bromo-2-fluoro-1-nitrobenzene using essentially the same procedure as described for Intermediate 40. $^1$H-NMR (500 MHz, CD$_3$Cl) δ 9.84 (s, 1H), 8.09-8.08 (m, 1H), 7.21-7.15 (m, 2H), 3.87 (s, 2H)

INTERMEDIATE 23

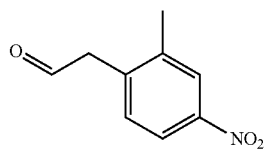

2-Methyl-4-nitrophenylacetaldehyde

The title compound was prepared from 1-Bromo-2-methyl-4-nitrobenzene using essentially the same procedure as described for Intermediate 40. $^1$H-NMR (500 MHz, CD$_3$Cl) δ 9.76 (s, 1H), 8.074 (s, 1H), 7.32-7.30 (m, 2H), 3.86 (s, 2H), 2.61 (s, 3H)

INTERMEDIATE 24

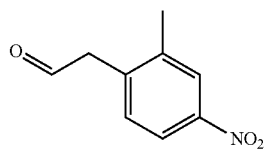

1-(2-Iodoethyl)-4-nitrobenzene

To a 0° C. solution of tiphenylphosphine (1.9 g, 7.2 mmol) and iidazole (489 mg, 7.18 mmol) in DCM (20 ml) was added iodine (1822 mg, 7.18 mmol) to form a solution. Small portions of 2-(4-ntrophenyl)ethanol (1.0 g, 6.0 mmol) was added to the suspension. TLC showed conversion to the desired product quickly. Hexane was added to the reaction to precipitate side products which were filtered off. The filtrate was concentrated in vacuo to obtain crude 1-(2-iodoethyl)-4-nitrobenzene, which was purified by silica gel flash chromatography using Hexane and EtOAc system. $^1$H-NMR (500 MHz, CD$_3$Cl) δ 8.22 (d, J=8.5 Hz, 2H), 7.40 (d, J=8.5 Hz, 2H), 3.41 (t, J=7.0 Hz, 2H), 3.32 (t, J=7.0 Hz, 2H).

INTERMEDIATE 25

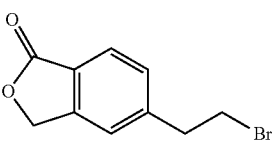

5-(2-Bromoethyl)-2-benzofuran-1(3H)-one

Step A: 5-Allyl-2-benzofuran-1(3H)-one

A 4-neck, 22-L, round bottom flask equipped with a mechanical stirrer, thermocouple, nitrogen bubbler, and condenser was charged with 5-bromophthalide (650 g, 3.0 mol), allyltri-n-butyltin (1200 g, 3.6 mol), palladium tetrakis triphenylphosphine (100 g, 0.089 mol), lithium chloride (250 g, 5.9 mol) and toluene (8.8 L). The mixture was evacuated and flushed with nitrogen 3 times and then was stirred at 100° C. for 4 hours. After slowly cooling to ambient temperature, the mixture was filtered and concentrated. The resulting solid was purified by silica gel column chromatography (heptane: ethyl acetate, 0→40%) to provide 5-allyl-2-benzofuran-1 (3H)-one.

Step B: 5-(2-Hydroxyethyl)-2-benzofuran-1(3H)-one 5-allyl-2-benzofuran-1(3H-one (1.53 g, 8.78 mmol) was dissolved in methanol (30 mL). THF was added to solubilize the starting material. The resulting mixture was cooled in a dry ice acetone bath (−78° C.) and ozone was bubbled into the reaction until the color of the mixture changed to orange. Nitrogen was bubbled into the reaction for one minute to remove the excess ozone. Sodium borohydride (0.65 g, 2.9 mmol) was added at −78° C., and the reaction mixture was allowed to warm to ambient temperature. The reaction mixture was concentrated part way and then taken up in ethyl acetate and water. The layers were separated and the organic layer was washed with brine, dried over magnesium sulfate, filtered, and concentrated to provide the title compound.

Step C: 5-(2-Bromoethyl)-2-benzofuran-1(3H)-one

To a solution of 5-(2-hydroxyethyl)-2-benzofuran-1(3H)-one (1.2 g, 6.8 mmol) in DCM at 0° C. was added carbon tetrabromide (2.3 g, 6.8 mmol), triphenylphosphine (1.8 g, 6.8 mmol), and imidazole (0.46 g, 6.8 mmol). The mixture was allowed to stir at 0° C. for 5 minutes, and then allowed to warm to RT and stir for 1.5 hours. The crude was concentrated and purified by silica gel chromatography (43% EtOAc with Hexanes) to obtain 5-(2-Bromoethyl)-2-benzofuran-1(3H)-one. LC-MS (IE, m/z): 241/243 (M+1)$^+$.

INTERMEDIATE 26

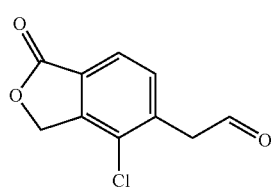

(4-chloro-1-oxo-1,3-dihydro-2-benzofuran-5-yl) acetaldehyde

Step A: methyl 3-amino-2-chlorobenzoate

To a solution of methyl 2-chloro-3-nitrobenzoate (2.1 g, 9.7 mmol) in methanol (100 mL) and THF (20 mL) was added zinc powder (1.9 g, 29 mmol), ammonium formate (3.1 g, 49 mmol), and a few drops of acetic acid. The mixture was allowed to stir at RT for 18 hours. Most of the volatiles were removed under reduced pressure. The residue was redissolved in EtOAc (200 mL), washed with brine, concentrated and purified by MPLC to provide methyl 3-amino-2-chlorobenzoate.

Step B: methyl 3-bromo-2-chlorobenzoate

To a solution of methyl 3-amino-2-chlorobenzoate (2.0 g, 11 mmol) in 48% HBr (10 mL) and water (20 mL) was added an aqueous solution of sodium nitrite (0.89 g, 13 mmol) at 0° C. The mixture was allowed to stir at 0° C. for 30 minutes before it was added into a suspension of copper(I) bromide (2.3 g, 16 mmol) in water (10 mL) and 48% HBr (5 mL) at 0° C. The reaction was allowed to warm to RT slowly, and then heated to 60° C. for 5 minutes. The product was extracted with DCM (100 mL×2). The extractions were combined, dried over sodium sulfate, adsorbed onto silica gel, and purified by MPLC to provide methyl 3-bromo-2-chlorobenzoate. LC-MS (IE, m/z): 251 [M+1]$^+$ Step C: (3-bromo-2-chlorophenyl)methanol To a solution of methyl 3-bromo-2-chlorobenzoate (1.9 g, 7.6 mmol) in THF (30 mL) was added Super Hydride (23 mL, 23 mmol) at 0° C. The reaction was allowed to stir for 16 hours. The reaction was diluted with EtOAc, washed with brine, dried over sodium sulfate, and purified by MPLC to provide (3-bromo-2-chlorophenyl)methanol. LC-MS (IE, m/z): 205 [M−17]$^+$;

Step D: 5-bromo-4-chloro-2-benzofuran-1(3H)-one

To a flask charged with (3-bromo-2-chlorophenyl)methanol (1.1 g, 4.8 mmol) and a stir bar was added thallium trifluoroacetate (2.9 g, 5.3 mmol) and TFA (6 mL). The mixture was allowed to stir at RT for 16 hours. The volatiles were removed under reduced pressure. The residue was pumped under high vacuum for 15 minutes before palladium (II) chloride (0.085 g, 0.48 mmol), magnesium oxide (0.39 g, 9.6 mmol), lithium chloride (0.20 g, 4.8 mmol), and ethanol (30 mL) were added. The mixture was stirred under an atmosphere of carbon mono-oxide until the reaction turned black. The reaction was diluted with DCM. The suspension was filtered through a pad of celite to remove the solids. The filtrate was adsorbed onto silica gel, and purified by MPLC to afford the title compound.

Step E: 5-allyl-4-chloro-2-benzofuran-1(3H)-one

To a flask charged with 5-bromo-4-chloro-2-benzofuran-1 (3H)-one (190 mg, 0.77 mmol) and a stir bar was added allyl tri-n-butyltin (0.36 mL, 1.2 mmol), PdCl$_2$(dppf)-DCM complex, lithium chloride (0.098 mg, 2.3 mmol), and toluene (5 mL). The flask was fitted with a condensor, purged three times with nitrogen, and heated to reflux for 6 hours. When LC showed complete reaction, the crude material was purified by MPLC to provide 5-allyl-4-chloro-2-benzofuran-1(3H)-one. LC-MS (IE, m/z): 209 [M+1]$^+$;

Step E: (4-chloro-1-oxo-1,3-dihydro-2-benzofuran-5-yl)acetaldehyde

Ozone was bubbled through a solution of 5-allyl-4-chloro-2-benzofuran-1(3H)-one (80 mg, 0.38 mmol) in MeOH at −78° C. until it turned light blue. After excess ozone was removed by bubbling nitrogen through the solution, dimethyl sulfide (0.57 mL, 7.7 mmol) was added into the reaction. The solution was allowed to warm to RT. The crude material was purified by MPLC to provide (4-chloro-1-oxo-1,3-dihydro-2-benzofuran-5-yl)acetaldehyde. LC-MS (IE, m/z): 211 [M+1]$^+$.

INTERMEDIATE 27

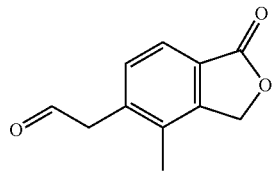

(4-Methyl-1-oxo-1,3-dihydro-2-benzofuran-5-yl)acetaldehyde

Step A: 4-methyl-5-prop-2-en-1-yl-2-benzofuran-1(3H)-one

To a flask charged with 5-Bromo-4-methyl-2-benzofuran-1(3H)-one (320 mg, 1.41 mmol) and a stir bar was added Allyl tri-n-butyltin (0.655 ml, 2.11 mmol), Pd(PPh$_3$)$_4$ (244 mg, 0.211 mmol), lithium chloride (179 mg, 4.23 mmol), and toluene (15 mL). The reaction was purged with nitrogen 2 times then was heated at reflux for 4 hours. The product was purified by silica gel chromatography to give the title compound.

Step B: (4-methyl-1-oxo-1,3-dihydro-2-benzofuran-5-yl)acetaldehyde

A solution of the above olefin (220 mg, 1.2 mmol) in MeOH (20 mL) was cooled to −78° C. To this solution was bubbled ozone until the reaction turned blue. Nitrogen was bubbled through the reaction to drive off excess ozone, followed by addition of DMS (0.870 mL, 11.7 mmol). The reaction was allowed to warm up to RT. The crude product was purified by flash chromatography to afford (4-methyl-1-oxo-1,3-dihydro-2-benzofuran-5-yl)acetaldehyde. $^1$H-NMR (500 MHz, CDCl$_3$) δ ppm 9.78 (s, 1H), 7.75 (d, J=7.5 Hz, 1H), 7.34 (d, J=7.5 Hz, 1H), 5.27 (s, 2H), 3.90 (s, 2H), 2.23 (s, 3H).

INTERMEDIATE 28

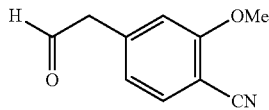

2-(Methyloxy)-4-(2-oxoethyl)benzonitrile

Step A: 2-(Methyloxy)-4-prop-2-en-1-ylbenzonitrile

To a 50 mL flask containing a stir bar were added 2-methoxy-4-bromobenzonitrile (0.30 g, 1.4 mmol), palladium tetrakis (82 mg, 0.071 mmol), allyltri-n-butyltin (0.88 mL, 2.8 mmol), and lithium chloride (0.120 g, 2.83 mmol). The resulting mixture was then dissolved in anhydrous toluene (16 mL); the flask was placed in an oil bath and heated at 130° C. LC as well as TLC (hexanes/EtOAc=1/0.3) indicated that reaction had gone to completion. The flask was taken out of the oil bath and cooled to room temperature. To the flask was poured EtOAc (40 mL) and the mixture was transferred into a reparatory funnel and washed with aqueous NaCl. The organic phase was dried over Na$_2$SO$_4$, filtered and concentrated to dryness. It was then dissolved in DCM and absorbed into silica gel. The silica gel was then loaded onto a silica column for separation with the solvent systems of hexanes/EtOAc (1/0.3); this gave 2-(methyloxy)-4-prop-2-en-1-ylbenzonitrile. LC-MS (IE, m/z): 174 [M+1]$^+$.

Step B: 2-(Methyloxy)-4-(2-oxoethyl)benzonitrile

To a 25 mL flask containing a stir bar was added compound 2-(methyloxy)-4-prop-2-en-1-ylbenzonitrile (0.15 g, 0.87 mmol) and MeOH (8 mL). The flask was placed in a cold bath of −78° C. Ozone was bubbled through the flask for about 10 min. followed by addition of dimethyl sulfide (1.5 mL, 24 mmol). The flask was taken out of the cold bath and stirred at room temperature for 1 h; LC indicated completion of the reaction. The reaction mixture was concentrated to dryness to give 2-(methyloxy)-4-(2-oxoethyl)benzonitrile. LC-MS (IE, m/z): 176 [M+1]$^+$.

INTERMEDIATE 29

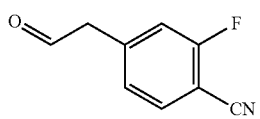

2-Fluoro-4-(2-oxoethyl)benzonitrile

Step A: Methyl (3-fluoro-4-hydroxyphenyl)acetate (3-Fluoro-4-hydroxy-phenyl)-acetic acid (25 g, 150 mmol) was dissolved in methanol (100 mL), and thionyl chloride (5 mL) was added dropwise to the solution. The solution was heated to 85° C. for 16 hours. The reaction mixture was allowed to cool and evaporated to dryness in vacuo. The residue was partitioned between ethyl acetate and saturated NaHCO$_3$. The organic layer was dried over MgSO$_4$, filtered, and the filtrate was evaporated to dryness under reduced pressure to yield the crude title compound as an off white solid (25.3 g). $^1$H NMR (500 MHz, CDCl$_3$): δ 7.07 (d, J=7.07 Hz, 1H), 7.00-6.97 (m, 2H), 3.74 (s, 3H), 3.73 (s, 2H).

Step B: Methyl (3-fluoro-4-{[(trifluoromethyl)sulfonyl]oxy}phenyl)acetate

The crude phenol [methyl (3-fluoro-4-hydroxyphenyl)acetate, 25.3 g] was dissolved in anhydrous dichloromethane (200 mL). 4-Dimethylaminopyridine (1.68 g) was added, followed by triethylamine (23.0 mL, 165 mmol). The solution was then cooled to in a dry ice and acetone bath while under nitrogen. Trifluoromethanesulfonic anhydride (27.9 mL, 165 mmol) was slowly added and the reaction mixture was allowed to warm to ambient temperature. The reaction mixture was then diluted with dichloromethane (200 mL) and washed with water (2×100 mL). The organic layer was dried over magnesium sulfate, filtered, and concentrated to dryness under reduced pressure and a cold water bath to yield the crude triflate. LC-MS (IE, m/z): 316 [M+1]$^+$.

Step C: Methyl (4-cyano-3-fluorophenyl)acetate

The crude triflate (43.4 g) was subsequently dissolved in anhydrous dimethylformamide (100 mL). Zinc cyanide (7.2 g, 78 mmol) was added, and the solution was purged thoroughly with nitrogen. Tetrakis(triphenylphosphine) palladium(0) (12 g, 14 mmol) was then added and the reaction mixture was heated to 80° C. for 4 h. After allowing cooling to ambient temperature and diluting with water (300 mL), ethyl acetate (500 mL) was added. The combined layers were filtered to remove any solids, the filtrate transferred to a reparatory funnel, and the layers separated. The aqueous layer was re-extracted with ethyl acetate (1×100 mL), the organic portions were combined and dried over magnesium sulfate. The dry organics were then filtered and evaporated to dryness under reduced pressure and excess dimethylformamide was removed by evaporation in vacuo at 65° C. for 1.5 h to yield the crude title compound (42 g). The crude product was purified through silica gel chromatography (ethyl acetate: hexanes=2:3) to yield the title nitrile. $^1$H NMR (500 MHz, CDCl$_3$): δ 7.62 (t, J=6.1 Hz, 1H), 7.23-7.21 (m, 2H), 3.76 (s, 3H), 3.73 (s, 2H). LC-MS (IE, m/z): 194 [M+1]$^+$.

Step D: 2-Fluoro-4-(2-hydroxyethyl)benzonitrile

LiBH$_4$ (1.94 mL, 3.88 mmol, 2 M in THF) was added to a stirred solution of methyl(4-cyano-3-fluorophenyl)acetate (0.50 g, 2.59 mmol) in THF (25 ml) at 0° C. The resulting solution was stirred for 12 h. Water (10 ml) was added, and the resulting solution was extracted with dichloromethane (2×50 ml). The combined organic layers were dried over MgSO$_4$, filtered, and evaporated under reduced pressure. The residue was purified by column chromatography eluting with EtOAc-Hexanes (7:3→1:1) to give the product as colorless oil. $^1$H NMR (500 MHz, CDCl$_3$) δ 7.60 (dd, J=7.4, J=7.1 Hz, 1H), 7.30 (s, 1H), 7.18 (dd, J=7.3, J=9.1 Hz, 1H), 3.95 (t, J=6.2 Hz, 2H), 2.93 (t, J=6.3 Hz, 2H).

Step E: 2-Fluoro-4-(2-oxoethyl)benzonitrile

To a stirred solution of 2-fluoro-4-(2-hydroxyethyl)benzonitrile (0.40 g, 2.4 mmol) in dry CH$_2$Cl$_2$ (20 mL) at 0° C. was added Dess-Martin periodinane (1.54 g, 3.6 mmol) in one portion. The mixture was stirred for 12 h at rt and quenched with a 1:1 mixture of saturated Na$_2$S$_2$O$_3$ (10 mL) and saturated NaHCO$_3$ (10 mL). The resulting mixture was diluted with CH$_2$Cl$_2$ (70 mL) and the layers were separated. The aqueous phase was extracted with CH$_2$Cl$_2$ (2×50 mL). The combined organic phases were washed with brine, dried (Na$_2$SO$_4$), and concentrated in vacuo to give crude aldehyde as colorless oil. The residue was used in the next step without further purification. LC-MS (IE, m/z): 164.1 [M+1]$^+$.

Intermediates described above may be referred to by their number preceded by "I-". For example, Intermediate 1 is shortened to I-1.

EXAMPLE 1

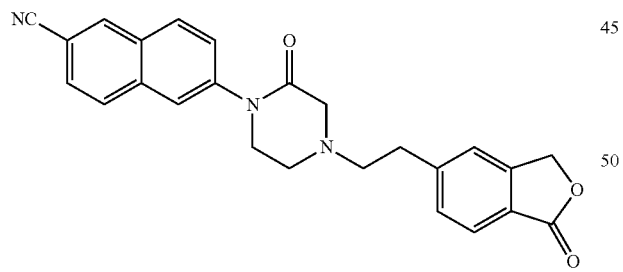

6-{2-Oxo-4-[2-(1-oxo-1,3-dihydro-2-benzofuran-5-yl)ethyl]piperazin-1-yl}naphthalene-2-carbonitrile To a 25 mL pear shaped flask charged with 6-(2-Oxopiperazin-1-yl)naphthalene-2-carbonitrile hydrochloride [I-5] (30 mg, 0.10 mmol) and a stir bar was added (1-Oxo-1,3-dihydro-2-benzofuran-5-yl)acetaldehyde [I-1] (28 mg, 0.16 mmol), sodium triacetocyborohydride (22 mg, 0.10 mmol), DCM, and a few drops of acetic acid. The mixture was allowed to stir at RT for 16 hours. The title product was purified by mass-directed reverse phase HPLC (AcCN-Water with 0.1% TFA). LC-MS (IE, m/z): 412 [M+1]$^+$.

EXAMPLE 2

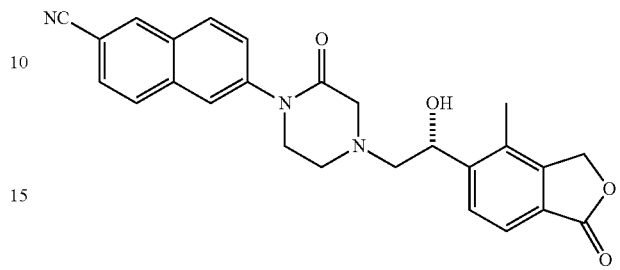

6-{4-[(2R)-2-Hydroxy-2-(4-methyl-1-oxo-1,3-dihydro-2-benzofuran-5-yl)ethyl]-2-oxopiperazin-1-yl}naphthalene-2-carbonitrile A mixture of 6-(2-Oxopiperazin-1-yl)naphthalene-2-carbonitrile (33 mg, 0.13 mmol) and 4-methyl-5-[(2R)-oxiran-2-yl]-2-benzofuran-1(3H)-one (38 mg, 0.20 mmol) in EtOH (2 mL) in a 5 mL microwave tube was heated to 148° C. for 1.5 hours. LC showed formation of the title product, which was purified by mass-directed reverse phase HPLC (AcCN-Water with 0.1% TFA). LC-MS (IE, m/z): 442 [M+1]$^+$.

EXAMPLE 3

Mixture of 2 Enantiomers

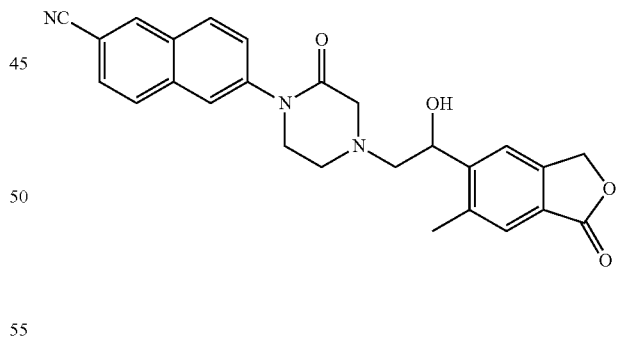

6-{4-[2-Hydroxy-2-(6-methyl-1-oxo-1,3-dihydro-2-benzofuran-5-yl)ethyl]-2-oxopiperazin-1-yl}naphthalene-2-carbonitrile A mixture of 6-(2-Oxopiperazin-1-yl)naphthalene-2-carbonitrile [I-5] (40 mg, 0.16 mmol) and 6-methyl-5-(oxiran-2-yl)-2-benzofuran-1(3H)-one [I-16] (30 mg, 0.16 mmol of the fast eluting isomer) in EtOH (1.5 mL) was heated to 140° C. for 1 hour. The reaction mixture was concentrated to dryness, and dissolved in MeOH, filtered and shot into Mass-directed HPLC for purification to give the title product. LC-MS (IE, m/z): 442 [M+1]+.

EXAMPLE 4

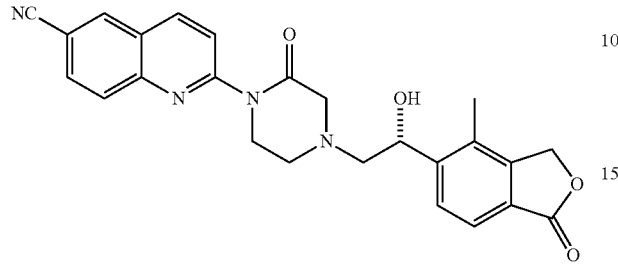

6-{4-[(2R)-2-Hydroxy-2-(4-methyl-1-oxo-1,3-dihydro-2-benzofuran-5-yl)ethyl]-2-oxopiperazin-1-yl}quinoline-2-carbonitrile A mixture of 2-(2-Oxopiperazin-1-yl)quinoline-6-carbonitrile [I-2] (20 mg, 0.079 mmol) and 4-methyl-5-[(2R)-oxiran-2-yl]-2-benzofuran-1(3H)-one (30 mg, 0.16 mmol) in EtOH (2 mL) was heated to 140° C. for 1 hour. The reaction mixture was concentrated to dryness, and dissolved in MeOH, filtered and shot into Mass-directed HPLC for purification to give the title product. LC-MS (IE, m/z): 443 [M+1]+.

EXAMPLE 5

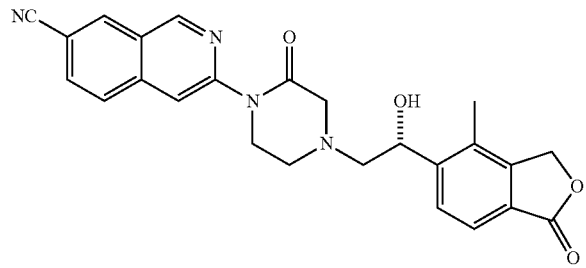 [SMILES: Cc1c([C@@H](O)CN2CCN(c3cc4ccc(C#N)cc4cn3)C(=O)C2)ccc2c1COC2=O]

3-{4-[(2R)-2-Hydroxy-2-(4-methyl-1-oxo-1,3-dihydro-2-benzofuran-5-yl)ethyl]-2-oxopiperazin-1-yl}isoquinoline-7-carbonitrile A mixture of 3-(2-oxopiperazin-1-yl)isoquinoline-7-carbonitrile [I-6] (20 mg, 0.079 mmol) and 4-methyl-5-[(2R)-oxiran-2-yl]-2-benzofuran-1(3H)-one (30 mg, 0.16 mmol) in EtOH (1 mL) in a 5 mL microwave tube was heated to 145° C. for 1.5 hours. LC showed formation of title product, which was purified by mass-directed reverse phase HPLC (AcCN-Water with 0.1% TFA). LC-MS (IE, m/z): 443 [M+1]+.

EXAMPLE 6

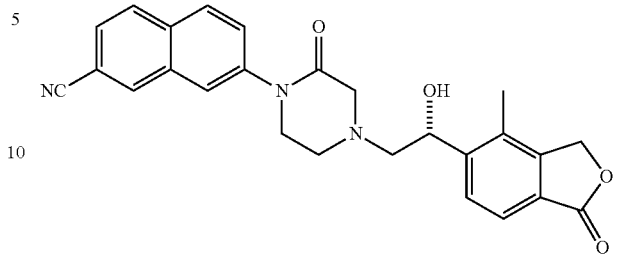

7-{4-[(2R)-2-Hydroxy-2-(4-methyl-1-oxo-1,3-dihydro-2-benzofuran-5-yl)ethyl]-2-oxopiperazin-1-yl}naphthalene-2-carbonitrile A mixture of 7-(2-oxopiperazin-1-yl)naphthalene-2-carbonitrile [I-7] (35 mg, 0.14 mmol) and 4-methyl-5-[(2R)-oxiran-2-yl]-2-benzofuran-1(3H)-one (40 mg, 0.21 mmol) in EtOH (2 mL) in a 5 mL microwave tube was heated to 145° C. for 2 hours. LC showed formation of the title product, which was purified by silica gel flash chromatography. LC-MS (IE, m/z): 442 [M+1]+.

EXAMPLE 7

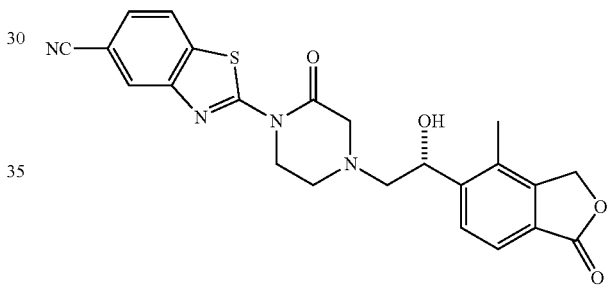

2-{4-[(2R)-2-Hydroxy-2-(4-methyl-1-oxo-1,3-dihydro-2-benzofuran-5-yl)ethyl]-2-oxopiperazin-1-yl}-1,3-benzothiazole-5-carbonitrile A mixture of 2-(2-Oxopiperazin-1-yl)-1,3-benzothiazole-5-carbonitrile [I-8] (25 mg, 0.10 mmol) and 4-methyl-5-[(2R)-oxiran-2-yl]-2-benzofuran-1(3H)-one (37 mg, 0.19 mmol) in EtOH (2 mL) in a 5 mL microwave tube was heated to 145° C. for 1.5 hours. LC showed formation of the title product, which was purified by silica gel flash chromatography. LC-MS (IE, m/z): 449 [M+1]+.

EXAMPLE 8

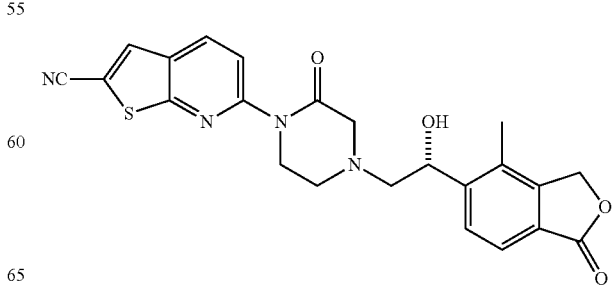

6-{4-[(2R)-2-Hydroxy-2-(4-methyl-1-oxo-1,3-dihydro-2-benzofuran-5-yl)ethyl]-2-oxopiperazin-1-yl}thieno-[2,3-b]pyridine-2-carbonitrile A mixture of 4-[(2R)-2-hydroxy-2-(4-methyl-1-oxo-1,3-dihydro-2-benzofuran-5-yl)ethyl]piperazin-2-one [I-10] (33 mg, 0.11 mmol), 6-chlorothieno[2,3-b]pyridine-2-carbonitrile [I-13] (22 mg, 0.11 mmol), $Pd_2(dba)_3$ (21 mg, 0.023 mmol), Xantphos (26 mg, 0.045 mmol), and $Cs_2CO_3$ (55 mg, 0.17 mmol) in dioxane (2 mL) was sealed in a microwave tube and purged three times with nitrogen. It was heated to 120° C. for 20 minutes in a microwave reactor. LC showed formation of the title product, which was purified by silica gel flash chromatography. LC-MS (IE, m/z): 449 [M+1]$^+$.

EXAMPLE 9

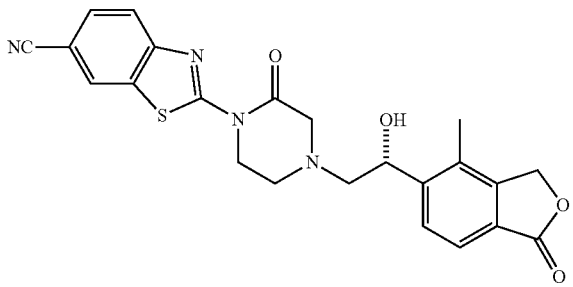 [SMILES: Cc1c([C@@H](O)CN2CCN(c3nc4ccc(C#N)cc4s3)C(=O)C2)ccc2c1COC2=O]

2-{4-[(2R)-2-Hydroxy-2-(4-methyl-1-oxo-1,3-dihydro-2-benzofuran-5-yl)ethyl]-2-oxopiperazin-1-yl}-1,3-benzothiazole-6-carbonitrile Step A 2-Chloro-1,3-benzothiazole-6-carbonitrile is commercially available or can be prepared as described in Example 268 of US Patent Publication No. US2009/019862.

Step B

A mixture of 4-[(2R)-2-hydroxy-2-(4-methyl-1-oxo-1,3-dihydro-2-benzofuran-5-yl)ethyl]piperazin-2-one [I-10] (30 mg, 0.10 mmol), 2-chloro-1,3-benzothiazole-6-carbonitrile (20 mg, 0.10 mmol), $Pd_2(dba)_3$ (19 mg, 0.021 mmol), Xantphos (24 mg, 0.041 mmol), and $Cs_2CO_3$ (50 mg, 0.16 mmol) in dioxane (2 mL) was sealed in a microwave tube and purged three times with nitrogen. It was heated to 120° C. for 10 minutes in a microwave reactor. LC showed formation of the title product, which was purified by silica gel flash chromatography. LC-MS (IE, m/z): 449 [M+1]$^+$.

EXAMPLE 10

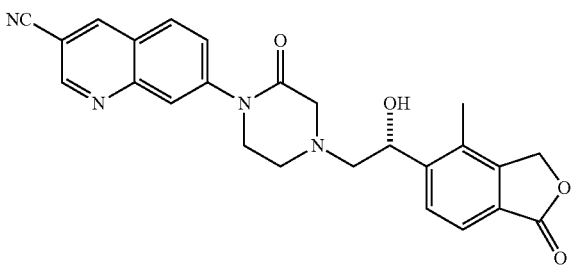 [SMILES: Cc1c([C@@H](O)CN2CCN(c3ccc4cc(C#N)cnc4c3)C(=O)C2)ccc2c1COC2=O]

7-{4-[(2R)-2-Hydroxy-2-(4-methyl-1-oxo-1,3-dihydro-2-benzofuran-5-yl)ethyl]-2-oxopiperazin-1-yl}quinoline-3-carbonitrile A mixture of 7-(2-oxopiperazin-1-yl)quinoline-3-carbonitrile [I-9] (20 mg, 0.079 mmol) and 4-methyl-5-[(2R)-oxiran-2-yl]-2-benzofuran-1(3H)-one (30 mg, 0.16 mmol) in EtOH (1.5 mL) in a 5 mL microwave tube was heated to 140° C. for 2 hours. LC showed formation of the title product, which was purified by mass-directed reverse phase HPLC (AcCN-Water with 0.1% TFA). LC-MS (IE, m/z): 443 [M+1]$^+$.

EXAMPLE 11

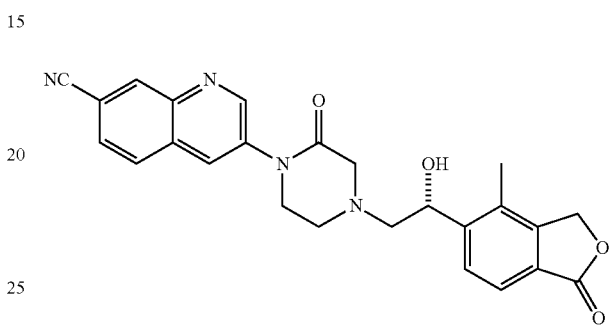

3-{4-[(2R)-2-Hydroxy-2-(4-methyl-1-oxo-1,3-dihydro-2-benzofuran-5-yl)ethyl]-2-oxopiperazin-1-yl}quinoline-7-carbonitrile A mixture of 3-(2-oxopiperazin-1-yl)quinoline-7-carbonitrile [I-4] (17 mg, 0.067 mmol) and 4-methyl-5-[(2R)-oxiran-2-yl]-2-benzofuran-1(3H)-one (19 mg, 0.10 mmol) in EtOH (1.5 mL) in a 5 mL microwave tube was heated to 140° C. for 1 hour. LC showed formation of the title product, which was purified by mass-directed reverse phase HPLC (AcCN-Water with 0.1% TFA). LC-MS (IE, m/z): 443 [M+1]$^+$.

EXAMPLE 12

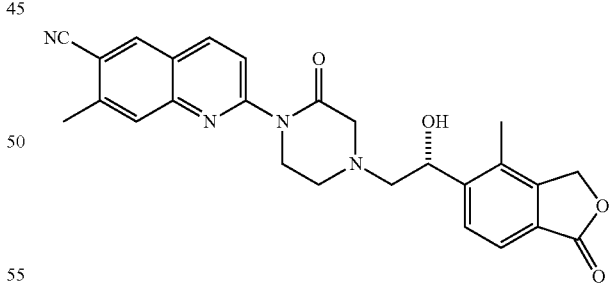

2-{4-[(2R)-2-Hydroxy-2-(4-methyl-1-oxo-1,3-dihydro-2-benzofuran-5-yl)ethyl]-2-oxopiperazin-1-yl}-7-methylquinoline-6-carbonitrile A mixture of 7-Methyl-2-(2-oxopiperazin-1-yl)quinoline-6-carbonitrile [I-3] (125 mg, 0.47 mmol) and 4-methyl-5-[(2R)-oxiran-2-yl]-2-benzofuran-1(3H)-one (134 mg, 0.70 mmol) in EtOH (1.5 mL) in a 5 mL microwave tube was heated to 140° C. for 20 minutes. LC showed formation of the desired product, which was purified by mass-directed reverse phase HPLC (AcCN-Water with 0.1% TFA). LC-MS (IE, m/z): 457 [M+1]+.

EXAMPLE 13

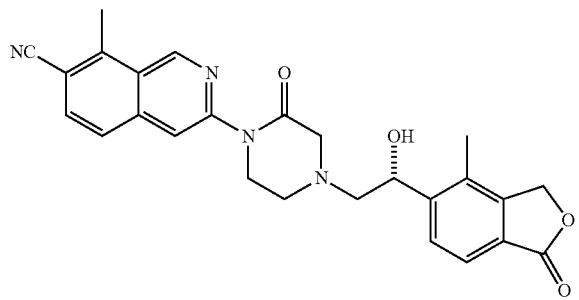 [SMILES: Cc1c([C@@H](O)CN2CCN(c3cc4ccc(C#N)c(C)c4cn3)C(=O)C2)ccc2c1COC2=O]

3-{4-[(2R)-2-Hydroxy-2-(4-methyl-1-oxo-1,3-dihydro-2-benzofuran-5-yl)ethyl]-2-oxopiperazin-1-yl}-8-methylisoquinoline-7-carbonitrile A mixture of 4-[(2R)-2-hydroxy-2-(4-methyl-1-oxo-1,3-dihydro-2-benzofuran-5-yl)ethyl]piperazin-2-one (26 mg, 0.089 mmol), 3-Chloro-8-methylisoquinoline-7-carbonitrile [I-12] (18 mg, 0.089 mmol), Pd$_2$(dba)$_3$ (16 mg, 0.017 mmol), Xantphos (21 mg, 0.036 mmol), and Cs$_2$CO$_3$ (40 mg, 0.12 mmol) in dioxane (4 mL) was sealed in a microwave tube and purged three times with nitrogen. It was heated to 100° C. for 10 minutes in a microwave reactor. LC showed formation of the desired product, which was purified by silica gel flash chromatography. LC-MS (IE, m/z): 457 [M+1]+.

EXAMPLE 14

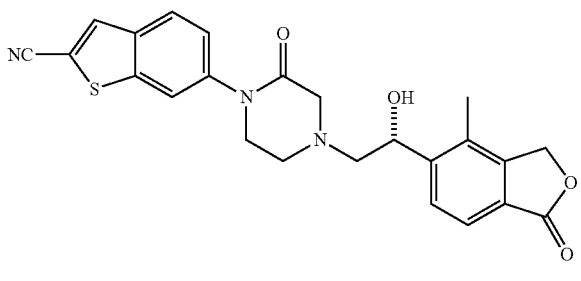

6-{4-[(2R)-2-Hydroxy-2-(4-methyl-1-oxo-1,3-dihydro-2-benzofuran-5-yl)ethyl]-2-oxopiperazin-1-yl}-1-benzothiophene-2-carbonitrile A mixture of 4-[(2R)-2-hydroxy-2-(4-methyl-1-oxo-1,3-dihydro-2-benzofuran-5-yl)ethyl]piperazin-2-one (50 mg, 0.17 mmol), 6-Bromo-1-benzothiophene-2-carbonitrile [I-11] (41 mg, 0.17 mmol), Pd$_2$(dba)$_3$ (32 mg, 0.034 mmol), Xantphos (40 mg, 0.069 mmol), and Cs$_2$CO$_3$ (84 mg, 0.26 mmol) in dioxane (1 mL) was sealed in a microwave tube and purged three times with nitrogen. It was heated to 120° C. for 20 minutes in a microwave reactor. LC showed formation of the desired product, which was purified by silica gel flash chromatography. LC-MS (IE, m/z): 448 [M+1]+.

EXAMPLE 15

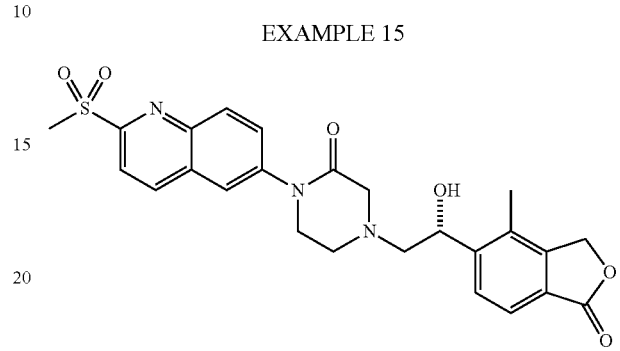

4-[(2R)-2-hydroxy-2-(4-methyl-1-oxo-1,3-dihydro-2-benzofuran-5-yl)ethyl]-1-[2-(methylsulfonyl)quinolin-6-yl]piperazin-2-one A mixture of 4-[(2R)-2-hydroxy-2-(4-methyl-1-oxo-1,3-dihydro-2-benzofuran-5-yl)ethyl]piperazin-2-one (66 mg, 0.23 mmol), 6-Bromo-2-(methylsulfonyl)quinoline [I-14] (65 mg, 0.23 mmol), Pd$_2$(dba)$_3$ (42 mg, 0.045 mmol), Xantphos (53 mg, 0.091 mmol), and Cs$_2$CO$_3$ (110 mg, 0.34 mmol) in DMF (5 mL) was sealed in a microwave tube and purged three times with nitrogen. It was heated to 120° C. for 10 minutes in a microwave reactor. LC showed formation of the product. The material was purified by silica gel flash chromatography, followed by crystallization to give the title product. LC-MS (IE, m/z): 496 [M+1]+.

The following Examples in Table 1 can be made from I-1

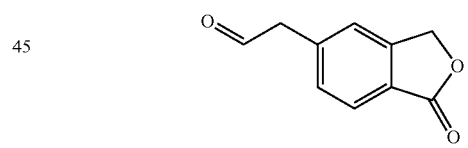

and the starting material also shown in the Table, using the synthetic procedures described above.

TABLE 1

| Example | Starting Material | Final Product |
|---|---|---|
| 16 | | |

TABLE 1-continued
| Example | Starting Material | Final Product |
|---------|------------------|---------------|
| 17 | | |
| 18 | | |
| 19 | | |
| 20 | | |
The following Examples in Table 2 can be made from I-16
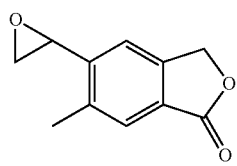
and the starting material also shown in the Table, using the synthetic procedures described above.

TABLE 2

| Example | Starting Material | Final Product |
|---|---|---|
| 21 | | |
| 22 | | |
| 23 | | |
| 24 | | |
| 25 | | |

The following Examples in Table 3 can be made from the intermediate starting materials also shown in the Table, using the synthetic procedures described above.

Calcium/Magnesium-free PBS. Add 5 mL of 1× trypsin (prepared in Ca/Mg Free PBS) to T-225 flask and return flask to 37° C./$CO_2$ incubator for 2-3 minutes. To dislodge the cell,

TABLE 3

| Example | Intermediate SM's | Final Product |
|---------|-------------------|---------------|
| 26 | [structures: 7-cyanoisoquinoline-piperazinone with NH; and 3-fluoro-4-nitrophenylacetaldehyde] | [structure: 7-cyanoisoquinoline-piperazinone-N-CH2CH2-(3-fluoro-4-nitrophenyl)] |
| 27 | [structures: 7-cyanoisoquinoline-piperazinone with NH; and 6-cyano-2-tetralone] | [structure: 7-cyanoisoquinoline-piperazinone-N-(6-cyanotetralin-2-yl)] |
| 28 | [structures: 7-cyanoisoquinoline-piperazinone with NH; and 3-methoxy-4-cyanophenylacetaldehyde] | [structure: 7-cyanoisoquinoline-piperazinone-N-CH2CH2-(3-methoxy-4-cyanophenyl)] |

The following Thallium Flux Assay was performed on the final product compounds in all the Examples. This assay makes use of the ability of thallium to permeate through open ROMK channels and increase the fluorescence of a dye previously loaded into the cells. Under control conditions, cells loaded with dye and exposed to thallium-containing medium display a time-dependent increase in fluorescence, the rate of which depends on number of functional channels. When cells are incubated in the presence of a channel inhibitor, the increase in fluorescence is attenuated in a concentration-dependent manner, and $IC_{50}$ values of inhibition by compounds can be accurately determined. This assay has been established with cell lines expressing either human, or rat ROMK channels, and operates in 384-well format.

Thallium Flux Assay

Cell Culture Conditions—

HEK293 cells stably expressing hROMK (h$K_{ir}$1.1) were grown at 37° C. in a 10% $CO_2$ humidified incubator in complete growth media: Dulbecco's Modified Eagle Medium supplemented with non-essential amino acids, Penicillin/Streptomycin/Glutamine, G418 and FBS. At >80% confluency, aspirate the media from the flask and rinse with 10 mL gently bang the side of the flask with your hand. Triturate the cells completely and then transfer the cells to 25 mL complete media. Centrifuge at 1,500 rpm for 6 min followed by resuspension in complete growth media and determine cell concentration. For typical re-seeding, 4E6 cells/T-225 flask will attain >80% confluency in 4 days. Under ideal growth conditions and appropriate tissue culture practices, this cell line is stable for 40-45 passages.

FluxOR Kit Components (Invitrogen F10017)
  FluxOR™ Reagent (Component A)
  FluxOR™ Assay Buffer (Component B)—10× Concentrate
  PowerLoad™ Concentrate (Component C)—100× Concentrate
  Probenecid (Component D)—Lyophilized sample is kept at −20° C. Water soluble, 100× after solubilization in 1 mL water. Store at 4° C.
  FluxOR Chloride—free Buffer (Component E)-5× Concentrate
  Potassium sulfate ($K_2SO_4$) Concentrate (Component F)—125 mM in water. Store at 4° C.
  Thallium sulfate ($Tl_2SO_4$) Concentrate (Component G)—50 mM in water. Store at 4° C.
  DMSO (dimethyl sulfoxide, Component H)—1 mL (100%)

Reagent Preparation: FluxOR Working Solutions
  1000× FluxOR™ Reagent: Reconstitute a vial of component A in 100 μl DMSO; Mix well; Store 10 μl aliquots at −20° C.
  1× FluxOR™ Assay Buffer: Dilute Component B 10-fold with water; Adjust pH to 7.4 with Hepes/NaOH; Filter and store at 4° C.
  Probenecid/Assay Buffer: 100 mL of 1× FluxOR™ Assay Buffer; 1 mL of reconstituted component D; Store at 4° C.
  Loading Buffer (per microplate): 10 μl 1000× FluxOR™ Reagent; 100 μl component C; 10 mL Probenecid/Assay Buffer
  Compound Buffer (per microplate): 20 mL Probenecid/Assay Buffer; 0.3 mM ouabain (10 mM ouabain in water can be stored in amber bottle/aluminum foil at room temperature); Test compound
  1× FluxOR™ Chloride-Free Buffer: Prepare 1× working solution in water. Can be stored at room temperature
  Stimulant Buffer (prepared at 5× final concentration in 1× FluxOR™ Chloride-Free Buffer): 7.5 mM Thallium sulfate and 0.75 mM Potassium sulfate (to give a final assay concentration of 3 mM Thallium/0.3 mM Potassium). Store at 4° C. when not in use. If kept sterile, this solution is good for months.

Assay Protocol—

The ROMK channel functional thallium flux assay is performed in 384 wells, using the FLIPR-Tetra instrument. HEK-hKir1.1 cells are seeded in Poly-D-Lysine microplates and kept in a 37° C.-10% $CO_2$ incubator overnight. On the day of the experiment, the growth media is replaced with the FluxOR™ reagent loading buffer and incubated, protected from light, at ambient temperature (23-25° C.) for 90 min. The loading buffer is replaced with assay buffer±test compound followed by 30 min incubation at ambient temperature, where the Thallium/Potassium stimulant is added to the microplate.

Step Protocol
1. Seed HEK-hKir1.1 cells (50 μl at 20,000 cells/well) in 384-well PDL coated Microplates
2. Allow cells to adhere overnight in humidified 37° C./10% $CO_2$ incubator
3. Completely remove cell growth media from microplate and replace with 25 μl loading buffer
4. Incubate Microplate at room temperature, protected form light, for 90 min
5. Remove loading buffer and replace with 25 μl 1× Assay Buffer±test compound.
6. Incubate microplate at room temperature, protected form light, for 30 min
7. At FLIPR-Tetra 384: Add stimulant (Thallium/Potassium) solution to microplate and monitor fluorescence. Excitation=400 nm, Emission=460 & 580 nm. Collect data for ~10 min.

Data Calculation—

The fluorescence intensity of wells containing 3 μM of a standard control ROMK inhibitor of the present invention is used to define the ROMK-sensitive component of thallium flux. Fluorescence in the presence of test compounds is normalized to control values to provide % fluorescence change. $IC_{50}$ values represent the concentration of compound that inhibits 50% of the ROMK thallium flux signal.

Assay Standard—

Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 μM in this assay. Alternatively, the control could be another compound (outside the scope of Formula I) that has an $IC_{50}$ potency in this assay of less than 1 μM.

Representative examples of data collected for compounds of the present invention using the Thallium Flux Assay are shown in Table 4 below. All of the final product compounds in Examples 1-15 were tested in the Thallium Flux Assay and had $IC_{50}$ results of 0.5 μM or less.

TABLE 4

| EXAMPLE # | Thallium Flux $IC_{50}$ (μM) |
|---|---|
| 1 | 0.06 |
| 2 | 0.05 |
| 3 | 0.07 |
| 4 | 0.16 |
| 5 | 0.08 |
| 6 | 0.09 |
| 7 | 0.04 |
| 8 | 0.16 |
| 9 | 0.09 |
| 10 | 0.21 |
| 11 | 0.14 |
| 12 | 0.08 |
| 13 | 0.15 |
| 14 | 0.16 |
| 15 | 0.22 |

While the invention has been described with reference to certain particular embodiments thereof, numerous alternative embodiments will be apparent to those skilled in the art from the teachings described herein. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:
1. A compound having structural Formula I:

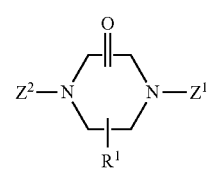

I or a pharmaceutically acceptable salt thereof wherein:
$Z^1$ is

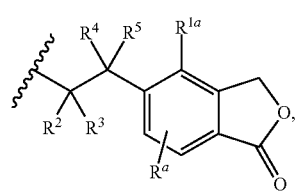

z1-a

-continued

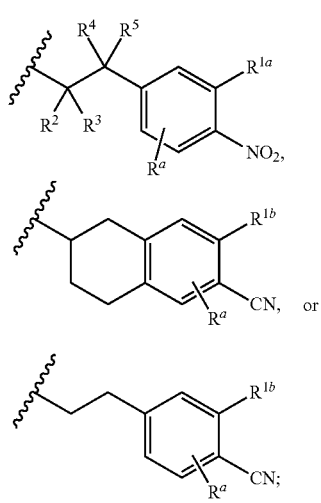

Z² is

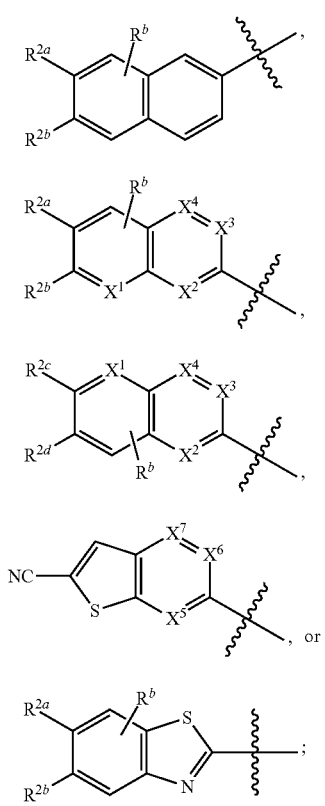

R¹ is —H, —CH₃, —CF₃, —CHF₂, —CH₂F or —CH₂OH;
R² is —H, oxo (=O) or —C₁₋₆alkyl;
R⁴ is —H, —OH, oxo or —C₁₋₆alkyl;
  provided that when R⁴ is —OH or oxo, then R² is not oxo;
R³ and R⁵ are each independently —H or —C₁₋₆alkyl;
  provided that R³ is absent when R² is oxo, and R⁵ is absent when R⁴ is oxo;
R¹ᵃ is —H, halo or —C₁₋₃alkyl;

R¹ᵇ is —H, halo, —C₁₋₃ alkyl, —O—C₁₋₃ alkyl or —COOC₁₋₃alkyl;
one of R²ᵃ and R²ᵇ is —CN and the other is —H or —C₁₋₃alkyl;
one of R²ᶜ and R²ᵈ is —SO₂—C₁₋₃alkyl and the other is —H or —C₁₋₃alkyl;
X¹, X², X³ and X⁴ are each independently CH or N, provided that only one of X¹, X², X³ or X⁴ is N;
X⁵, X⁶ and X⁷ are each independently CH or N, provided that only one of X⁵, X⁶ or X⁷ is N; and
Rᵃ and Rᵇ are each independently —H, halo, —C₁₋₃alkyl, —O—C₁₋₃alkyl or —COOC₁₋₃alkyl.

2. The compound of claim 1 or a pharmaceutically acceptable salt thereof having structural Formula II:

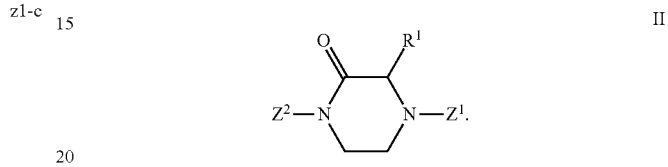

3. The compound of claim 1 or a pharmaceutically acceptable salt thereof wherein Z¹ is z1-a.

4. The compound of claim 3 or a pharmaceutically acceptable salt thereof wherein R², R³ and R⁵ are each —H, and R⁴ is —H, —OH or oxo.

5. The compound of claim 1 or a pharmaceutically acceptable salt thereof wherein Z¹ is z1-b.

6. The compound of claim 5 or a pharmaceutically acceptable salt thereof wherein R², R³ and R⁵ are each —H, and R⁴ is —H, —OH or oxo.

7. The compound of claim 1 or a pharmaceutically acceptable salt thereof wherein Z¹ is

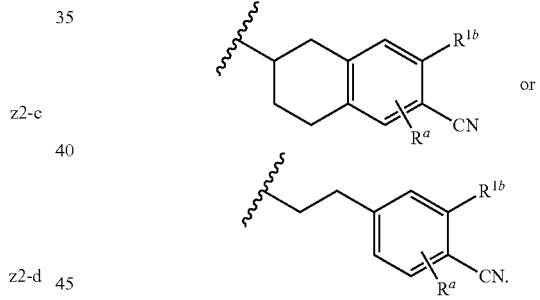

8. The compound of claim 7 or a pharmaceutically acceptable salt thereof wherein Z¹ is

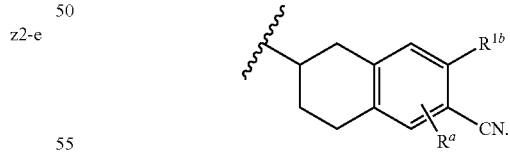

9. The compound of claim 7 or a pharmaceutically acceptable salt thereof wherein Z¹ is

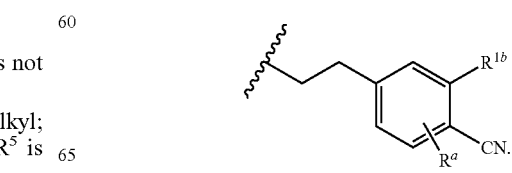

10. The compound of claim 1 which is
- 6-{2-oxo-4-[2-(1-oxo-1,3-dihydro-2-benzofuran-5-yl)ethyl]piperazin-1-yl}naphthalene-2-carbonitrile;
- 6-{4-[(2R)-2-Hydroxy-2-(4-methyl-1-oxo-1,3-dihydro-2-benzofuran-5-yl)ethyl]-2-oxopiperazin-1-yl}naphthalene-2-carbonitrile;
- 6-{4-[2-Hydroxy-2-(6-methyl-1-oxo-1,3-dihydro-2-benzofuran-5-yl)ethyl]-2-oxopiperazin-1-yl}naphthalene-2-carbonitrile;
- 2-{4-[(2R)-2-Hydroxy-2-(4-methyl-1-oxo-1,3-dihydro-2-benzofuran-5-yl)ethyl]-2-oxopiperazin-1-yl}-1,3-benzothiazole-5-carbonitrile; or
- 2-{4-[(2R)-2-Hydroxy-2-(4-methyl-1-oxo-1,3-dihydro-2-benzofuran-5-yl)ethyl]-2-oxopiperazin-1-yl}-7-methylquinoline-6-carbonitrile;

or a pharmaceutically acceptable salt thereof.

11. A pharmaceutical composition comprised of a compound of claim 1 and a pharmaceutically acceptable carrier.

12. The pharmaceutical composition of claim 11 further comprising one or more additional active agent selected from losartan, valsartan, candesartan, olmesartan, telmesartan, eprosartan, irbesartan, azilsartan, hydrochlorothiazide, amlodipine, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, trandolapril, amiloride, spironolactone, eplerenone, triamterene or acetazolamide or a pharmaceutically acceptable salt thereof.

13. A method for causing diueresis, natriuresis or both, comprising administering a compound of claim 1 in a therapeutically effective amount to a patient in need thereof.

14. A method for the treatment of one or more disorders selected from hypertension, acute heart failure, and chronic heart failure, pulmonary arterial hypertension comprising administering a compound of claim 1 in a therapeutically effective amount as appropriate, to a patient in need thereof.

* * * * *